(12) United States Patent
Mikoshiba et al.

(10) Patent No.: US 7,217,701 B2
(45) Date of Patent: May 15, 2007

(54) INTRACELLULAR CALCIUM CONCENTRATION INCREASE INHIBITORS

(75) Inventors: Katsuhiko Mikoshiba, Tokyo (JP); Hirohide Iwasaki, Aichi (JP); Takayuki Maruyama, Osaka (JP); Shin-ichi Hamano, Osaka (JP)

(73) Assignee: Katsuhiko Mikoshiba, Tokyo (JP)

( * ) Notice: Subject to any disclaimer, the term of this patent is extended or adjusted under 35 U.S.C. 154(b) by 340 days.

(21) Appl. No.: 10/492,150

(22) PCT Filed: Oct. 10, 2002

(86) PCT No.: PCT/JP02/10534

§ 371 (c)(1),
(2), (4) Date: Apr. 9, 2004

(87) PCT Pub. No.: WO03/033002

PCT Pub. Date: Apr. 24, 2003

(65) Prior Publication Data

US 2004/0259842 A1    Dec. 23, 2004

(30) Foreign Application Priority Data

Oct. 11, 2001   (JP) .............................. 2001/313402

(51) Int. Cl.
  *A61K 31/69*   (2006.01)
  *C07F 5/02*    (2006.01)
(52) U.S. Cl. ............................................. 514/64; 556/7
(58) Field of Classification Search ................ 514/64; 556/7
See application file for complete search history.

(56) References Cited

U.S. PATENT DOCUMENTS 3,397,228 A    8/1968   Brownstein

FOREIGN PATENT DOCUMENTS

| WO | 0059880 | 10/2000 |
| WO | 0127107 | 4/2001 |
| WO | 0238140 | 6/2002 |

OTHER PUBLICATIONS

Holzapfel et al., 1965, CAS: 63:89008.*
Lapkin et al., 1963, CAS: 58:27392.*
Dobrydneva, Yuliya et al., "2-aminoethoxydiphenyl borate directly inhibits store-operated calcium entry channels in human platelets," Molecular Pharmacology, Sep. 2001, vol. 60, No. 3, pp. 541-552.
Kukkonen, J.P. et al., "2-aminoethoxydiphenyl borate reveals heterogeneity in receptor-activated Ca2+ discharge and store-operated Ca2+ influx," Cell Calcium, Aug. 2001, vol. 30, No. 2, pp. 117-129.
Missiaen, L. et al, 2-Aminoethoxydiphenyl borate affects the inositol 1,4,5-trisphosphate receptor, the intracellular Ca2+ pump and the non-specific Ca2+ leak from the non-mitochondrial Ca2+ stores in permeabilized A7r5 cells,' Cell Calcium, Feb. 2001, vol. 29, No. 2, pp. 111-116.
Wu, Jie et al., "2-Aminoethoxydiphenyl borate modulates kinetics of intracellular Ca2+ signals mediated by inositol 1 4,5-trisphosphate-sensitive Ca2+ stores in single pancreatic acinar cells of mouse," Molecular Pharmacology, 2000, vol. 58, No. 6, pp. 1368-1374.
Maruyama, Takayuki et al., "2APB, 2-aminoethoxydiphenyl borate, a membrane-penetrable modulator of Ins(1,4,5)P3-induced Ca2+ release," Journal of Biochemistry (Tokyo), 1997, vol. 122, No. 3, pp. 498-505.
Reilly, T.M. et al., "Effect of thrombin inhibitors on platelet functions: aomparative analysis of DuP 714 and hirudin," Blood Coagulation & Febrinolysis, 1992, vol. 3, No. 5, pp. 513-517.
Chiu, Anrew T. et al., "Inhibition of thrombin-platelet reactions by DuP714," Biochemical and Biophysical Research Communications, 1991, vol. 179, No. 3, pp. 1500-1508.
International Search Report mailed Jan. 28, 2003.
Brief Report—"Capacitative Calcium Deficits and Elevated Luminal Calcium Content in Mutant Presenilin-1 Knockin Mice"—Malcolm A. Leissring et al; The Rockefeller University Press, 0021-9525/2000/05/793/5, the Journal of Cell Biology, vol. 149, No. 4, May 15, 2000 793-797.
"Presenilin-Mediated Modulation of Capacitative Calcium Entry"—Andrew S. Yoo et al—Neuron, vol. 27, 561-572, Sep. 2000, copyright 2000 by Cell Press.

* cited by examiner

*Primary Examiner*—Kamal A. Gaeed
*Assistant Examiner*—Rei-tsang Shiao
(74) *Attorney, Agent, or Firm*—Stevens, Davis, Miller & Mosher, LLP

(57) ABSTRACT

An intracellular calcium concentration increase inhibitor containing as the active ingredient (1) a boron compound represented by the formula (I).

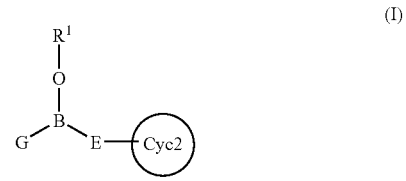

(I)

The compound represented by the formula (I) inhibits the increase of the intracellular calcium concentration, and therefore it is deemed to be useful as an agent for the prophylaxis and/or treatment of platelet aggregation, ischemic diseases in hearts and brains, immune deficiency diseases, allorgosis, bronchial asthma, hypertension, cerebrovascular spasm, various renal diseases, pancreatitis, Alzheimer's disease, etc.

4 Claims, No Drawings

INTRACELLULAR CALCIUM CONCENTRATION INCREASE INHIBITORS

This is a 371 of PCT/JP02/10534 filed on Oct. 10, 2002.

TECHNICAL FIELD

The present invention relates to an intracellular calcium concentration increase inhibitor.

Particularly, the present invention relates to an intracellular calcium concentration increase inhibitor containing as the active ingredient (1) a boron compound represented by the formula (I) and nontoxic salts thereof,

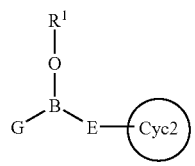

and (2) novel boron compounds selected from the following (1) to (94) or nontoxic salts therof:

(1) (3-chloro-4-methylphenyl)(4-benzyloxymethylphenyl)borate,
(2) (2-diethylaminocarbonylphenyl)phenylborate,
(3) (4-chlorophenyl)(4-benzyloxymethylphenyl)borate,
(4) (4-chlorophenyl)(4-(4-methoxybenzyloxymethyl)phenyl)borate,
(5) (4-chlorophenyl)[4-(1,2,3,4-tetrahydronaphtho-1-yloxymethyl)phenyl]borate,
(6) (4-chlorophenyl)(4-(2-phenylethoxy)methylphenyl)borate,
(7) (4-chlorophenyl)[4-(cyclohexyloxymethyl)phenyl]borate,
(8) (4-chlorophenyl)[4-(butoxymethyl)phenyl]borate,
(9) (1,1'-biphenyl-4-yl)[4-(benzyloxymethyl)phenyl]borate,
(10) (4-chlorophenyl)[3-(benzyloxymethyl)phenyl]borate,
(11) (3,5-dichlorophenyl)(4-benzyloxymethylphenyl)borate,
(12) (4-bromophenyl)(4-(benzyloxymethyl)phenyl)borate,
(13) (4-chlorophenyl)[4-(2-(phenylaminocarbonyloxy)ethyl)phenyl]borate,
(14) (4-chlorophenyl)[4-(2-(methoxycarbonyloxy)ethyl)phenyl]borate,
(15) (4-chlorophenyl)[4-(2-((2-methyl-4-nitrophenyl)aminocarbonyloxy)ethyl)phenyl]borate,
(16) (4-chlorophenyl)[4-(2-((3,5-di(methoxycarbonyl)phenyl)aminocarbonyloxy)ethyl)phenyl]borate,
(17) (4-chlorophenyl)[4-(2-(1-ethoxycarbonyl-2-methylpropylcarbamoyloxy)ethyl)phenyl]borate,
(18) bis[2-(hydroxyphenylboryl)benzyl]ether,
(19) 1,4-bis(4-(hydroxyphenylboryl)phenoxy)butane,
(20) bis[4-(hydroxyphenylboryl)benzyl]ether,
(21) bis(3-chloro-4-methylphenyl)borate,
(22) bis[4-(2-(methoxycarbonyl)vinyl)phenyl]borate,
(23) 2-cyclohexylaminoethyl bis(3-chloro-4-methylphenyl)borate,
(24) 2-aminoethyl bis(4-trifluoromethylphenyl)borate,
(25) 2-aminoethyl dicyclopentylborate,
(26) 2-aminoethyl bis(4-chloro-2-methylphenyl)borate,
(27) 2-aminoethyl bis(4-dimethylaminosulfonylphenyl)borate,
(28) 2-aminoethyl bis(2-naphthyl)borate,
(29) 2-aminoethyl bis(4-chloro-3-methylphenyl)borate,
(30) 2-aminoethyl bis(3-chloro-4-methylphenyl)borate,
(31) 2-aminoethyl bis(3,5-dichlorophenyl)borate,
(32) 2-pyridylmethyl bis(3-chloro-4-methylphenyl)borate,
(33) 2-dimethylaminoethyl bis(3-chloro-4-methylphenyl)borate,
(34) 1-methyl-2-aminoethyl bis(3-chloro-4-methylphenyl)borate,
(35) 2-(phenylamino)ethyl bis(3-chloro-4-methylphenyl)borate,
(36) 2-amino-4-guanidino-1-oxobutyl bis(4-chlorophenyl)borate,
(37) 2-(benzylamino)ethyl bis(3-chloro-4-methylphenyl)borate,
(38) 3-(benzyl-1,2,3-triazol-4-yl)methyl bis(3-chloro-4-methylphenyl)borate,
(39) 2-phenyl-2-aminoethyl bis(3-chloro-4-methylphenyl)borate,
(40) 2-(piperazin-1-yl)ethyl bis(3-chloro-4-methylphenyl)borate,
(41) 2-(butylamino)ethyl bis(3-chloro-4-methylphenyl)borate,
(42) 1-phenyl-1-(2-pyridyl)methyl bis(3-chloro-4-methylphenyl)borate,
(43) 2-amino-2-(methoxycarbonyl)ethyl bis(4-chlorophenyl)borate,
(44) 1-benzyl-2-(methyamino)ethyl bis(3-chloro-4-methylphenyl)borate,
(45) 1-phenyl-2-aminoethyl bis(3-chloro-4-methylphenyl)borate,
(46) 1-(4-chlorophenoxymethyl)-2-(methylamino)ethyl bis(3-chloro-4-methylphenyl)borate,
(47) 1-phenyl-2-(1-(ethoxycarbonyl)-piperidine-4-ylamino)ethyl bis(3-chloro-4-methylphenyl)borate,
(48) 1-(methylaminomethyl)nonyl bis(3-chloro-4-methylphenyl)borate,
(49) 3-phenyl-1-(2-pyridyl)propyl bis(3-chloro-4-methylphenyl)borate,
(50) cis-3-phenyl-1-(2-pyridyl)-2-propenyl bis(3-chloro-4-methylphenyl)borate,
(51) 1-(5-methylimidazol-4-yl)-1-phenylmethyl bis(3-chloro-4-methylphenyl)borate,
(52) 1-(2-imidazolyl)-1-phenylmethyl bis(3-chloro-4-methylphenyl)borate,
(53) 1-(2-pyridyl)ethyl bis(3-chloro-4-methylphenyl)borate,
(54) 1-(2-pyridyl)-2-propenyl bis(3-chloro-4-methylphenyl)borate,
(55) 1-methyl-1-(2-pyridyl)ethyl bis(3-chloro-4-methylphenyl)borate,
(56) 1-phenyl-1-(2-aminophenyl)methyl bis(3-chloro-4-methylphenyl)borate,
(57) (1S,2R)-1,2-diphenyl-2-aminoethyl bis(3-chloro-4-methylphenyl)borate,
(58) (1R,2S)-1,2-diphenyl-2-aminoethyl bis(3-chloro-4-methylphenyl)borate,
(59) 1-phenyl-1-(pyrazin-2-yl)methyl bis(3-chloro-4-methylphenyl)borate,
(60) 1-(dimethylaminomethyl)-2-dimethylaminoethyl bis(3-chloro-4-methylphenyl)borate,
(61) 1-(pyrazol-3-yl)-1-phenylmethyl bis(3-chloro-4-methylphenyl)borate,
(62) 1-(4-trifluoromethylphenyl)-1-(2-pyridyl)methyl bis(3-chloro-4-methylphenyl)borate,
(63) 1-(4-acetylamino)phenyl-1-(2-pyridyl)methyl bis(3-chloro-4-methylphenyl)borate,
(64) 2-aminoethyl bis(4-chloro-3-trifluoromethylphenyl)borate,

(65) 1-(3-chloropyridin-2-yl)-1-phenylmethyl bis(3-chloro-4-methylphenyl)borate,
(66) 2-aminoethyl bis(3,5-di(trifluoromethyl)phenyl)borate,
(67) 2-aminoethyl bis(3,4,5-trifluorophenyl)borate,
(68) 2-aminoethyl bis(2,3,4-trifluorophenyl)borate,
(69) 2-aminoethyl bis(3-chloro-4-(1,1-dimethylethyl)phenyl)borate,
(70) 1-(4-nitropyridin-2-yl)-1-phenylmethyl bis(3-chloro-4-methylphenyl)borate,
(71) 1-(4-bromopyridin-2-yl)-1-phenylmethyl bis(3-chloro-4-methylphenyl)borate,
(72) 5,6,7,8-tetrahydroquinolin-8-yl bis(3-chloro-4-methylphenyl)borate,
(73) 2-aminoethyl (4-chlorophenyl)(4-chloro-2-methoxyphenyl)borate,
(74) 2-aminoethyl (4-chlorophenyl)(1-naphthyl)borate,
(75) 2-aminoethyl (4-chlorophenyl)(1,1'-biphenyl-4-yl)borate,
(76) 2-aminoethyl (4-chlorophenyl)(3-chloro-4-phenoxymethyl)phenylborate,
(77) 2-aminoethyl (4-chlorophenyl)(benzothiazol-2-yl)borate,
(78) 2-aminoethyl (4-chlorophenyl)(4-methylnaphthyl-1-yl)borate,
(79) 2-aminoethyl (3-phenylpropyl)phenylborate,
(80) 2-aminoethyl (3,3-diphenylpropyl)phenylborate,
(81) 2-aminoethyl (2-phenoxyphenyl)phenylborate,
(82) 2-aminoethyl (4-vinylphenyl)(3,4-dichlorophenyl)borate,
(83) 2-aminoethyl (4-bromophenyl)(4-chlorophenyl)borate,
(84) 2-aminoethyl (4-chlorophenyl)(4-(1,1'-dimethylethyl)phenyl)borate,
(85) 2-aminoethyl (4-chlorophenyl)(4-iodophenyl)borate,
(86) 2-aminoethyl (4-chlorophenyl)(1,1'-biphenyl-2-yl)borate,
(87) 2-aminoethyl (3-pyridyl)phenylborate,
(88) 2-aminoethyl (3-pyridyl)(4-chlorophenyl)borate,
(89) bis[2-[(2-aminoethoxy)phenylboryl]benzyl]ether,
(90) bis[4-[(2-aminoethoxy)phenylboryl]benzyl]ether,
(91) [4-[(2-aminoethoxy)phenylboryl]benzyl][2-[4-[(2-aminoethoxy)phenylboryl]phenyl]ethyl]ether,
(92) [2-[(2-aminoethoxy)phenylboryl]benzyl][2-[4-[(2-aminoethoxy)phenylboryl]phenyl]ethyl]ether,
(93) 10H-phenoxaborin-10-ol,
(94) 1,3-bis(4-chlorophenyl)-1,3-dihydro-2,1-benzoxaborole

BACKGROUND OF THE INVENTION

Cells show a wide variety of physiology in responding to extracellular stimuli such as neurotransmitter, hormone and a growth factor. A calcium ion plays an important role in this regard as a messenger of intracellular signaling. The main source of the calcium is the intracellular calcium store and extracellular liquid. Calcium is released from the intracellular calcium store via inositol 1,4,5-trisphosphate ($IP_3$) receptor as the second messenger, or ryanodine receptor which is insensitive to $IP_3$ but releases calcium along with the increase of the intracellular calcium concentration.

As the intracellular second messenger, $IP_3$ carries out $IP_3$-induced Ca release (IICR), i.e., induces the release of a calcium ion from the intracellular calcium ion pool. $IP_3$ receptor is a channel for releasing the intracellular calcium ion, which is activated by the integration with $IP_3$. The $IP_3$ receptor forms a gene family, and is diverse in its function, tissue- or cell-specific expression and intracellular localization, and plays an essential important role in vital functions.

It is known that $IP_3$ is produced in a pathway activating a various receptors coupled with G-protein activity or in a pathway activating a various receptors coupled with tyrosine kinase activity. Phospoholipase C, which was activated in the above pathway, decomposes phosphatidylinositol 4,5-bisphosphate ($PIP_2$) into two second messengers, i.e., $IP_3$ and diacylglycerol (DG). $IP_3$ binds to an $IP_3$ receptor existing in the intracellular calcium store and has calcium released. On the other hand, DG activates protein kinase C with the released calcium and controls various types of physiology.

It is known that a various channels are concerned with the influx of the calcium ion from the extracellular fluid. The channels can be divided broadly into a voltage-dependent channel which functions depending on the membrane potential and a channel which functions independently from the potential. As a channel of the latter, a neurotransmitter receptor having calcium permeabirelity (e.g., NMDA receptor) is known. Recently, attention has been drawn to a calcium permeability channel which functions by the activation of G-protein coupled receptor and tyrosine kinase type receptor, and receptor activated calcium channel (RACC). RACC includes a capacitative calcium entry (CCE) channel, second messenger operated channel and G-protein operated channel.

A CCE channel is activated by the release and depletion of calcium ion from the intracellular calcium store, and makes extracellular calcium ions flow and reload into the intracellular calcium store. From this, CCE channels are also called store operated channels (SOCs).

The presence of the channel is established electrophysiologically in nonexcitatory cells such as immunocytes, vascular endothelial cells and thrombocytes, and the channel is known as a main calicium entry pathway for the nonexcitatory cells. However, its molecular substance has not been made clear. Moreover, the mechanisms of the channel in recognition of the depletion of the intracellular calcium store and in activation are also uncertain.

However, from the following experiments and the like, the fact is verified that the capacitative calcium entry and the calcium release from the intracellular calcium store wherein the $IP_3$ is concerned as mentioned above, play an important role in the expression of cell functions.

That is,
(1) When a thrombocyte is stimulated by thromboxane $A_2$ and thrombin, $IP_3$-mediated aggregation is caused and thrombus is formed, leading to ischemic diseases in hearts and brains.
    On this occasion, it is known that the capacitative calcium entry consequent upon the $IP_3$-induced Ca release (IICR) is essential to the thrombocyte aggregation (Biochimica et Biophysica Acta, 1082, 219–238 (1991); Platelets, 11(4), 215–21(2000)).
(2) Helper T (Th1) cells of the subset 1 in T-lymphocytes produce and secrete cytokines such as interleukin 2 (IL-2) and interferon γ and express IL-2 receptors. On this occasion, to start the transcription of the IL-2 genes, it is necessary for the NF-AT as a transcription promoter to become active and make transition to the nuclei. It is known that the increase of the intracellular calcium concentration owing to the capacitative calcium entry is essential for the activation of NF-AT (J. Cell Biol., 131(3), 655–67(1995)).
(3) $IP_3$ produced by the stimuli of leukotriene $D_4$ ($LTD_4$) and angiotensin II causes calcium release, which makes bronchial smooth muscle and vascular smooth muscle contract, and causes asthma, hypertension, cerebrovascular spasm, etc. It is known that the capacitative calcium entry is essential on this occasion (J. Pharm. Exp. Ther., 244, 508–515 (1987); *Protein Nucleic Acid Enzyme,* 36, 885–895 (1991); J. Membr. Biol., 155(1), 61–73(1997)).

(4) In exocrine pancreatic cells, the intracellular calcium concentration increases via $IP_3$ by stimuli of such as cholecystokinin and acetycholine, which causes abnormal secretion of protease and leads to pancreatitis. It is known that the capacitative calcium entry is essential on this occasion (Pharmacology & Toxicology, 68, 83–87 (1991); Proc. Natl. Acad. Sci. USA, 97(24), 13126–13131(2000)).

(5) Leukotriene $B_4$ ($LTB_4$) produced by neutrophils increases the intracellular calcium concentration via $IP_3$, causes neutrophil migration to inflammation sites and exaggerates the inflammation (ANN. NY. ACAD. Sci., 524, 187–195 (1988)). In the myocardial infarction, production of $LTB_4$ is also concernedwith the expansion of the necrotic layer (J. Pharm. Exp. Ther., 228, 510–522 (1983)).

(6) In kidneys, stimuli of such as angiotensin II and bradykinin increases mesangium cells together with the $IP_3$ production, which causes a type of glomerulonephritis. $IP_3$ is also concerned with other various renal diseases (Metabolism, 27, 413–425 (1990)).

Recently, the possibility has come into clear that the capacitative calcium entry takes an important function not only in the above nonexcitatory cells but also in nerve cells. For example, it is known that presenilin known as a gene causing familial Alzheimer's disease has a function as y-secretase which cuts amyloid protein precursor. When presenilin induced with point mutation discovered in the patient of familial Alzheimer's disease is expressed in cultured cells, it was proved that the capacitative calcium entry functions abnormally (Neuron, 27(3), 561–72(2000)). The experiment using the primary cultured cells derived from a mouse whose presenilin genes were destroyed also proved the abnormal function of the capacitative calcium entry (J. Cell Biol., 149(4), 793–8(2000)).

As mentioned above, the endogenous calcium and capacitative calcium entry are deeply linked to various diseases.

Accordingly, as an endogenous calcium release inhibitor or a capacitative calcium entry inhibitor has a function inhibiting the increase of the intracellular calcium concentration, it is deemed to be useful as an agent for the prophylaxis and/or treatment of platelet aggregation, immune deficiency diseases, allergosis, ischemic diseases in hearts and brains, bronchial asthma, hypertension, cerebrovascular spasm, various renal diseases, pancreatitis, Alzheimer's disease, etc.

The specification of Japanese Patent No. 2987727 discloses that 2-aminoethyl diphenylborinate and tetraphenylboroxane(tetraphenyldiboroxide) having an inhibitory effect on calcium release from the endogenous calcium store by the mechanisms of $IP_3$-induced Ca release (IICR) and calcium induced Ca release (CICR).

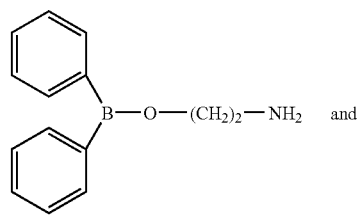

and

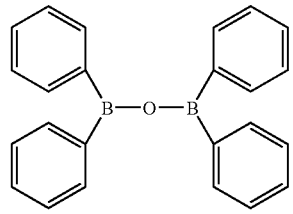

Also, it is described that 2-aminoethyl diphenylborinate has an inhibitory action on SOCs through an inhibitory action on $IP_3$ receptors (Science, 287, 1647–1651(2000)).

Moreover, the specification of WO02/38140 describes that bis-1-oxaquinolizidine, xestospongin C, xestospongin A, Araguspongin B and the like are useful as an inhibitor of calcium channels mediated by $IP_3$ receptors.

However, pharmaceutical agents have not yet been found for prophylaxis and/or treatment of various diseases by decreasing the concentration of the intracellular calcium which has been abnormally increased by the activation of $IP_3$ receptors or capacitative calcium entry.

DISCLOSURE OF THE INVENTION

As a result of intensive investigations to find out a compound to inhibit the endogenous calcium release and/or a compound to inhibit the capacitative calcium entry, the present inventors have found that the boron compound represented by the formula (I) accomplishes the purpose. The present invention has been accomplished based on this finding.

That is, the present invention relates to an intracellular calcium concentration increase inhibitor containing as the active ingredient (1) a boron compound represented by the formula (I) and nontoxic salts thereof

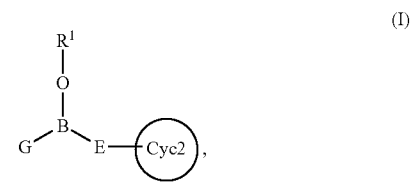

(I)

wherein $R^1$ is (1) a hydrogen atom;
(2) —$(CH_2)_n$—$NR^2R^3$, wherein n represents an integer of 1 to 3, $R^2$ and $R^3$ each independently represent, a hydrogen atom, C1–4 alkyl, mono-cyclic C5–6 carboring, C1–4 alkyl substituted with mono-cyclic C5–6 carboring, or mono-cyclic 5–6 membered heteroring,
wherein the carbon atom of —$(CH_2)_n$— may be substituted with 1 to 2 $R^4$, and the carboring and heteroring may be further substituted with 1 to 2 $R^7$,
$R^4$ is (a) C1–8 alkyl, (b) carboxyl, (c) C1–4 alkoxycarbonyl, (d) keto, (e) mono-cyclic C5–6 carboring, (f) guanidino(C1–2)alkyl, (g) C1–6 alkyl substituted with mono-cyclic C5–6 carboring, (h) C1–2 alkyl substituted with 4-chlorophenoxy, or (i) C1–4 alkyl substituted with di (C1–4 alkyl)amino;
(3) C1–6 alkyl or C2–6 alkenyl substituted with mono-cyclic C5–6 carboring, wherein the carboring may be substituted with 1 to 5 $R^7$, and the C1–6 alkyl or C2–6 alkenyl may be further substituted with 1 to 2 $R^{10}$;

(4) C1–6 alkyl or C2–6 alkenyl substituted with mono-cyclic 5–6 membered heteroring, wherein the heteroring may be substituted with 1 to 5 $R^7$, and the C1–6 alkyl or C2–6 alkenyl may be further substituted with 1 to 2 $R^{10}$, $R^{10}$ represents C1–4 alkyl or C2–4 alkenyl;

(5) —$CHR^5R^6$, wherein $R^5$ and $R^6$ independently represent
  (i) mono-cyclic C5–6 carboring,
  (ii) mono-cyclic 5–6 membered heteroring,
  (iii) C1–6 alkyl or C2–6 alkenyl substituted with mono-cyclic C5–6 carboring, or
  (iv) C1–6 alkyl or C2–6 alkenyl substituted with mono-cyclic 5–6 membered heteroring,
  wherein the carboring and heteroring may further be substituted with 1 to 5 $R^7$; or (6) 5,6,7,8-tetrahydroquinolin-8-yl;

$R^7$ represents (a) C1–4 alkyl, (b) C1–4 alkoxy, (c) a halogen atom, (d) —$CF_3$, (e) nitro, (f) mono-cyclic C5–6 carboring, (g) C1–4 alkyl substituted with mono-cyclic C5–6 carboring, (h) amino, (i) —NHCO(C1–4 alkyl), or (j) C1–4 alkoxycarbonyl; G represents Cyc1 or hydroxy;

Cyc1 represents mono- or bi-cyclic C5–10 carboring, or mono- or bi-cyclic 5–10 membered heteroring, wherein the carboring and heteroring may be substituted with 1 to 5 $R^8$;

Cyc2 represents mono- or bi-cyclic C5–10 carboring, or mono- or bi-cyclic 5–10 membered heteroring, wherein the carboring and heteroring may be substituted with 1 to 5 $R^9$;

$R^8$ and $R^9$ independently represents
(a) C1–4 alkyl,
(b) C2–4 alkenyl,
(c) C1–4 alkoxy,
(d) a halogen atom,
(e) —$CF_3$,
(f) C1–4 alkylthio,
(g) amino,
(h) (C1–4 alkyl)amino,
(i) di(C1–4 alkyl)amino,
(j) formyl,
(k) phenyl,
(l) phenoxy,
(m) hydroxy(C1–2)alkyl,
(n) (mono- or bi-cyclic C5–10 carboring)-O—(C1–2)alkyl,
(o) C1–4 alkoxycarbonylvinyl,
(p) C1–2 alkyl substituted with a group selected from —O—(C1–2 alkylene)-phenyl, wherein phenyl may be substituted with 1 to 3 C1–4 alkoxy, —O—CONH-phenyl, wherein phenyl may be substituted with 1 to 3 C1–4 alkyl, nitro or C1–4 alkoxycarbonyl, or —O—CONH—(C1–4) alkyl, wherein alkyl may be substituted with 1 to 3 C1–4 alkyl, carboxyl or C1–4 alkoxycarbonyl,
(q) phenylthio,
(r) —$CON(C1–4\ alkyl)_2$,
(s) —$SO_2N(C1–4\ alkyl)_2$,
(t) C1–4 alkoxy(C1–2)alkyl,
(u) C1–4 alkoxycarbonyloxy(C1–2)alkyl, (v)

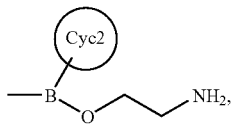

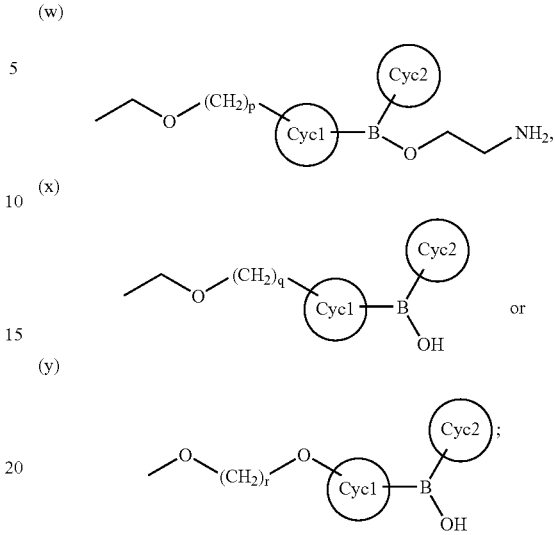

in $R^8$ and $R^9$, the carboring, phenyl, cyc1 and cyc2 may be substituted with 1 to 2 $R^7$, and $R^8$ together with $R^9$ may represent —O—, and $R^9$ together with $R^{10}$ may further represent a single bond;

p represents an integer of 1 to 4;
q represents an integer of 1 to 4;
r represents an integer of 1 to 4;
E represents a single bond or C1–4 alkylene substituted with mono-cyclic C5–6 carboring or non-substituted C1–4 alkylene; except 2-aminoethyl diphenylborinate;

and (2) novel boron compounds selected from the following (1) to (94) or nontoxic salts therof:

(1) (3-chloro-4-methylphenyl)(4-benzyloxymethylphenyl)borate,
(2) (2-diethylaminocarbonylphenyl)phenylborate,
(3) (4-chlorophenyl)(4-benzyloxymethylphenyl)borate,
(4) (4-chlorophenyl)(4-(4-methoxybenzyloxymethyl)phenyl)borate,
(5) (4-chlorophenyl)[4-(1,2,3,4-tetrahydronaphtho-1-yloxymethyl)phenyl]borate,
(6) (4-chlorophenyl)(4-(2-phenylethoxy)methylphenyl)borate,
(7) (4-chlorophenyl)[4-(cyclohexyloxymethyl)phenyl]borate,
(8) (4-chlorophenyl)[4-(butoxymethyl)phenyl]borate,
(9) (1,1'-biphenyl-4-yl)[4-(benzyloxymethyl)phenyl]borate,
(10) (4-chlorophenyl)[3-(benzyloxymethyl)phenyl]borate,
(11) (3,5-dichlorophenyl)(4-benzyloxymethylphenyl)borate,
(12) (4-bromophenyl)(4-(benzyloxymethyl)phenyl)borate,
(13) (4-chlorophenyl)[4-(2-(phenylaminocarbonyloxy)ethyl)phenyl]borate,
(14) (4-chlorophenyl)[4-(2-(methoxycarbonyloxy)ethyl)phenyl]borate,
(15) (4-chlorophenyl)[4-(2-((2-methyl-4-nitrophenyl)aminocarbonyloxy)ethyl)phenyl]borate,
(16) (4-chlorophenyl)[4-(2-((3,5-di(methoxycarbonyl)phenyl)aminocarbonyloxy)ethyl)phenyl]borate,
(17) (4-chlorophenyl)[4-(2-(1-ethoxycarbonyl-2-methylpropylcarbamoyloxy)ethyl)phenyl]borate,
(18) bis[2-(hydroxyphenylboryl)benzyl]ether,
(19) 1,4-bis(4-(hydroxyphenylboryl)phenoxy)butane,

(20) bis[4-(hydroxyphenylboryl)benzyl]ether,
(21) bis(3-chloro-4-methylphenyl)borate,
(22) bis[4-(2-(methoxycarbonyl)vinyl)phenyl]borate,
(23) 2-cyclohexylaminoethyl bis(3-chloro-4-methylphenyl)borate,
(24) 2-aminoethyl bis(4-trifluoromethylphenyl)borate,
(25) 2-aminoethyl dicyclopentylborate,
(26) 2-aminoethyl bis(4-chloro-2-methylphenyl)borate,
(27) 2-aminoethyl bis(4-dimethylaminosulfonylphenyl)borate,
(28) 2-aminoethyl bis(2-naphthyl)borate,
(29) 2-aminoethyl bis(4-chloro-3-methylphenyl)borate,
(30) 2-aminoethyl bis(3-chloro-4-methylphenyl)borate,
(31) 2-aminoethyl bis(3,5-dichlorophenyl)borate,
(32) 2-pyridylmethyl bis(3-chloro-4-methylphenyl)borate,
(33) 2-dimethylaminoethyl bis(3-chloro-4-methylphenyl)borate,
(34) 1-methyl-2-aminoethyl bis(3-chloro-4-methylphenyl)borate,
(35) 2-(phenylamino)ethyl bis(3-chloro-4-methylphenyl)borate,
(36) 2-amino-4-guanidino-1-oxobutyl bis(4-chlorophenyl)borate,
(37) 2-(benzylamino)ethyl bis(3-chloro-4-methylphenyl)borate,
(38) 3-(benzyl-1,2,3-triazol-4-yl)methyl bis(3-chloro-4-methylphenyl)borate,
(39) 2-phenyl-2-aminoethyl bis(3-chloro-4-methylphenyl)borate,
(40) 2-(piperazin-1-yl)ethyl bis(3-chloro-4-methylphenyl)borate,
(41) 2-(butylamino)ethyl bis(3-chloro-4-methylphenyl)borate,
(42) 1-phenyl-1-(2-pyridyl)methyl bis(3-chloro-4-methylphenyl)borate,
(43) 2-amino-2-(methoxycarbonyl)ethyl bis(4-chlorophenyl)borate,
(44) 1-benzyl-2-(methyamino)ethyl bis(3-chloro-4-methylphenyl)borate,
(45) 1-phenyl-2-aminoethyl bis(3-chloro-4-methylphenyl)borate,
(46) 1-(4-chlorophenoxymethyl)-2-(methylamino)ethyl bis(3-chloro-4-methylphenyl)borate,
(47) 1-phenyl-2-(1-(ethoxycarbonyl)-piperidine-4-ylamino)ethyl bis(3-chloro-4-methylphenyl)borate,
(48) 1-(methylaminomethyl)nonyl bis(3-chloro-4-methylphenyl)borate,
(49) 3-phenyl-1-(2-pyridyl)propyl bis(3-chloro-4-methylphenyl)borate,
(50) cis-3-phenyl-1-(2-pyridyl)-2-propenyl bis(3-chloro-4-methylphenyl)borate,
(51) 1-(5-methylimidazol-4-yl)-1-phenylmethyl bis(3-chloro-4-methylphenyl)borate,
(52) 1-(2-imidazolyl)-1-phenylmethyl bis(3-chloro-4-methylphenyl)borate,
(53) 1-(2-pyridyl)ethyl bis(3-chloro-4-methylphenyl)borate,
(54) 1-(2-pyridyl)-2-propenyl bis(3-chloro-4-methylphenyl)borate,
(55) 1-methyl-1-(2-pyridyl)ethyl bis(3-chloro-4-methylphenyl)borate,
(56) 1-phenyl-1-(2-aminophenyl)methyl bis(3-chloro-4-methylphenyl)borate,
(57) (1S,2R)-1,2-diphenyl-2-aminoethyl bis(3-chloro-4-methylphenyl)borate,
(58) (1R,2S)-1,2-diphenyl-2-aminoethyl bis(3-chloro-4-methylphenyl)borate,
(59) 1-phenyl-1-(pyrazin-2-yl)methyl bis(3-chloro-4-methylphenyl)borate,
(60) 1-(dimethylaminomethyl)-2-dimethylaminoethyl bis(3-chloro-4-methylphenyl)borate,
(61) 1-(pyrazol-3-yl)-1-phenylmethyl bis(3-chloro-4-methylphenyl)borate,
(62) 1-(4-trifluoromethylphenyl)-1-(2-pyridyl)methyl bis(3-chloro-4-methylphenyl)borate,
(63) 1-(4-acetylamino)phenyl-1-(2-pyridyl)methyl bis(3-chloro-4-methylphenyl)borate,
(64) 2-aminoethyl bis(4-chloro-3-trifluoromethylphenyl)borate,
(65) 1-(3-chloropyridin-2-yl)-1-phenylmethyl bis(3-chloro-4-methylphenyl)borate,
(66) 2-aminoethyl bis(3,5-di(trifluoromethyl)phenyl)borate,
(67) 2-aminoethyl bis(3,4,5-trifluorophenyl)borate,
(68) 2-aminoethyl bis(2,3,4-trifluorophenyl)borate,
(69) 2-aminoethyl bis(3-chloro-4-(1,1-dimethylethyl)phenyl)borate,
(70) 1-(4-nitropyridin-2-yl)-1-phenylmethyl bis(3-chloro-4-methylphenyl)borate,
(71) 1-(4-bromopyridin-2-yl)-1-phenylmethyl bis(3-chloro-4-methylphenyl)borate,
(72) 5,6,7,8-tetrahydroquinolin-8-yl bis(3-chloro-4-methylphenyl)borate,
(73) 2-aminoethyl (4-chlorophenyl)(4-chloro-2-methoxyphenyl)borate,
(74) 2-aminoethyl (4-chlorophenyl)(1-naphthyl)borate,
(75) 2-aminoethyl (4-chlorophenyl)(1,1'-biphenyl-4-yl)borate,
(76) 2-aminoethyl (4-chlorophenyl)(3-chloro-4-phenoxymethyl)phenylborate,
(77) 2-aminoethyl (4-chlorophenyl)(benzothiazol-2-yl)borate,
(78) 2-aminoethyl (4-chlorophenyl)(4-methylnaphthyl-1-yl)borate,
(79) 2-aminoethyl (3-phenylpropyl)phenylborate,
(80) 2-aminoethyl (3,3-diphenylpropyl)phenylborate,
(81) 2-aminoethyl (2-phenoxyphenyl)phenylborate,
(82) 2-aminoethyl (4-vinylphenyl)(3,4-dichlorophenyl)borate,
(83) 2-aminoethyl (4-bromophenyl)(4-chlorophenyl)borate,
(84) 2-aminoethyl (4-chlorophenyl)(4-(1,1'-dimethylethyl)phenyl)borate,
(85) 2-aminoethyl (4-chlorophenyl)(4-iodophenyl)borate,
(86) 2-aminoethyl (4-chlorophenyl)(1,1'-biphenyl-2-yl)borate,
(87) 2-aminoethyl (3-pyridyl)phenylborate,
(88) 2-aminoethyl (3-pyridyl)(4-chlorophenyl)borate,
(89) bis[2-[(2-aminoethoxy)phenylboryl]benzyl]ether,
(90) bis[4-[(2-aminoethoxy)phenylboryl]benzyl]ether,
(91) [4-[(2-aminoethoxy)phenylboryl]benzyl][2-[4-[(2-aminoethoxy)phenylboryl]phenyl]ethyl]ether,
(92) [2-[(2-aminoethoxy)phenylboryl]benzyl][2-[4-[(2-aminoethoxy)phenylboryl]phenyl]ethyl]ether,
(93) 10H-phenoxaborin-10-ol,
(94) 1,3-bis(4-chlorophenyl)-1,3-dihydro-2,1-benzoxaborole.

In the present invention, the inhibition of increase of the intracellular calcium concentration indicates the inhibition of the abnormal increase of the intracellular calcium concentration. Its mechanism is to inhibit the endogenous calcium release and/or capacitative calcium entry, more specifically, the inhibition of the endogenous calcium release, the inhibition of the capacitative calcium entry or the both of them.

As the endogenous calcium release inhibitor, antagonistic agents of IP$_3$ receptors are desirable.

In the present specification, C1–2 alkyl is methyl and ethyl.

In the present specification, (C1–2) alkyl is methyl and ethyl.

In the present specification, C1–4 alkyl is methyl, ethyl, propyl, butyl and isomers thereof.

In the present specification, C1–6 alkyl is methyl, ethyl, propyl, butyl, pentyl, hexyl and isomers thereof.

In the present specification, C1–8 alkyl is methyl, ethyl, propyl, butyl, pentyl, hexyl, heptyl, octyl and isomers thereof.

In the present specification, C1–4 alkoxy is methoxy, ethoxy, propoxy, butoxy and isomers thereof.

In the present specification, C1–4 alkylthio is methylthio, ethylthio, propylthio, butylthio and isomers thereof.

In the present specification, C2–4 alkenyl is ethenyl, propenyl, butenyl and isomers thereof.

In the present specification, C2–6 alkenyl is ethenyl, propenyl, butenyl, pentenyl, hexenyl and isomers thereof.

In the present specification, C1–2 alkylene is methylene and ethylene.

In the presentspecification, C1–4 alkylene ismethylene, ethylene, trimethylene, tetramethylene and isomers thereof.

In the present specification, C1–6 alkylene is methylene, ethylene, trimethylene, tetramethylene, pentamethylene, hexamethylene and isomers thereof.

In the present specification, C2–6 alkenylene is ethenylen, propenylen, butenylen, pentenylen, hexenylen and isomers thereof.

In the present specification, halogen atommeans chlorine, fluorine, bromine and iodine atom.

In the present specification, mono-cyclic C5–6 carboring is mono-cyclic C5–6 carboaryl or partially or completely saturated one thereof. For example, cyclopentane, cyclohexane, cyclopentene, cyclohexene, cyclopentadiene, cyclohexadiene, benzene are included.

In the presentspecification, C1–4 alkyl substituted with mono-cyclic C5–6 carboring is C1–4 alkyl substituted with mono-cyclic C5–6 carboaryl or partially or completely saturated one thereof. For example, C1–4 alkyl substituted with cyclopentane, cyclohexane, cyclopentene, cyclohexene, cyclopentadiene, cyclohexadiene, benzene are included.

In the present specification, a 5–6 membered mono-cyclic heterorring is 5–6 membered mono-cyclic heteroaryl containing 1 to 4 of nitrogen atom(s), 1 to 2 of oxygen atom(s) and/or 1 of sulfur atom or partially or completely saturated one thereof. For example, pyrrole, imidazole, triazole, tetrazole, pyrazole, pyridine, pyrazine, pyrimidine, pyridazine, furan, pyrane, thiophene, thiine, oxazole, isoxazole, thiazole, isothiazole, pyrroline, pyrrolidine, imidazoline, imidazolidine, triazoline, triazolidine, tetrazoline, tetrazolidine, pyrazoline, pyrazolidine, piperidine, piperazine, perhydropyrimidine and perhydropyridazine are included.

In the present specification, mono- or bi-cyclic C5–10 carboring is mono- or bi-cyclic C5–10 carboaryl or partially or completely saturated one thereof. For example, cyclopentane, cyclohexane, cycloheptane, cyclooctane, cyclononane, cyclodecane, cyclopentene, cyclohexene, cycloheptane, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene ring are included.

In the present specification, a 5–10 membered mono-or bi-cyclic heterorring is 5–10 membered mono- or bi-cyclic heteroaryl containing 1 to 4 of nitrogen atom(s), 1 oxygen atom and/or 1 of sulfur atom or partially or completely saturated one thereof. For example, pyrrole, imidazole, triazole, tetrazole, pyrazole, pyridine, pyrazine, pyrimidine, pyridazine, furan, pyrane, thiophene, thiine, oxazole, isoxazole, thiazole, isothiazole, indole, isoindole, benzofuran, isobenzofuran, benzothiophene, isobenzothiophene, indazole, quinoline, isoquinoline, quinoxaline, quinazoline, cinnoline, benzoxazole, benzothiazole, benzoimidazole, chromene, indoline, isoindoline, dihydrobenzofuran, dihydrobenzothiophene, dihydroindazole, tetrahydroquinoline, tetrahydroisoquinoline, tetrahydroquinoxaline, tetrahydroquinazoline, and tetrahydrocinnoline, etc.

The specific compounds to be used in the present invention include (1) (3-chloro-4-methylphenyl)(4-benzyloxymethylphenyl)borate,
(2) (2-diethylaminocarbonylphenyl)phenylborate,
(3) (4-chlorophenyl)(4-benzyloxymethylphenyl)borate,
(4) (4-chlorophenyl)(4-(4-methoxybenzyloxymethyl)phenyl)borate,
(5) (4-chlorophenyl)[4-(1,2,3,4-tetrahydronaphtho-1-yloxymethyl)phenyl]borate,
(6) (4-chlorophenyl)(4-(2-phenylethoxy)methylphenyl)borate,
(7) (4-chlorophenyl)[4-(cyclohexyloxymethyl)phenyl]borate,
(8) (4-chlorophenyl)[4-(butoxymethyl)phenyl]borate,
(9) (1,1'-biphenyl-4-yl)[4-(benzyloxymethyl)phenyl]borate,
(10) (4-chlorophenyl)[3-(benzyloxymethyl)phenyl]borate,
(11) (3,5-dichlorophenyl)(4-benzyloxymethylphenyl)borate,
(12) (4-bromophenyl)(4-(benzyloxymethyl)phenyl)borate,
(13) (4-chlorophenyl)[4-(2-(phenylaminocarbonyloxy)ethyl)phenyl]borate,
(14) (4-chlorophenyl)[4-(2-(methoxycarbonyloxy)ethyl)phenyl]borate,
(15) (4-chlorophenyl)[4-(2-((2-methyl-4-nitrophenyl)aminocarbonyloxy)ethyl)phenyl]borate,
(16) (4-chlorophenyl)[4-(2-((3,5-di(methoxycarbonyl)phenyl)aminocarbonyloxy)ethyl)phenyl]borate,
(17) (4-chlorophenyl)[4-(2-(1-ethoxycarbonyl-2-methylpropylcarbamoyloxy)ethyl)phenyl]borate,
(18) bis[2-(hydroxyphenylboryl)benzyl]ether,
(19) 1,4-bis(4-(hydroxyphenylboryl)phenoxy)butane,
(20) bis[4-(hydroxyphenylboryl)benzyl]ether,
(21) bis(3-chloro-4-methylphenyl)borate,
(22) bis[4-(2-(methoxycarbonyl)vinyl)phenyl]borate,
(23) 2-cyclohexylaminoethyl bis(3-chloro-4-methylphenyl)borate,
(24) 2-aminoethyl bis(4-trifluoromethylphenyl)borate,
(25) 2-aminoethyl dicyclopentylborate,
(26) 2-aminoethyl bis(4-chloro-2-methylphenyl)borate,
(27) 2-aminoethyl bis(4-dimethylaminosulfonylphenyl)borate,
(28) 2-aminoethyl bis(2-naphthyl)borate,
(29) 2-aminoethyl bis(4-chloro-3-methylphenyl)borate,
(30) 2-aminoethyl bis(3-chloro-4-methylphenyl)borate,
(31) 2-aminoethyl bis(3,5-dichlorophenyl)borate,
(32) 2-pyridylmethyl bis(3-chloro-4-methylphenyl)borate,
(33) 2-dimethylaminoethyl bis(3-chloro-4-methylphenyl)borate,
(34) 1-methyl-2-aminoethyl bis(3-chloro-4-methylphenyl)borate,
(35) 2-(phenylamino)ethyl bis(3-chloro-4-methylphenyl)borate,

(36) 2-amino-4-guanidino-1-oxobutyl bis(4-chlorophenyl)borate,
(37) 2-(benzylamino)ethyl bis(3-chloro-4-methylphenyl)borate,
(38) 3-(benzyl-1,2,3-triazol-4-yl)methyl bis(3-chloro-4-methylphenyl)borate,
(39) 2-phenyl-2-aminoethyl bis(3-chloro-4-methylphenyl)borate,
(40) 2-(piperazin-1-yl)ethyl bis(3-chloro-4-methylphenyl)borate,
(41) 2-(butylamino)ethyl bis(3-chloro-4-methylphenyl)borate,
(42) 1-phenyl-1-(2-pyridyl)methyl bis(3-chloro-4-methylphenyl)borate,
(43) 2-amino-2-(methoxycarbonyl)ethyl bis(4-chlorophenyl)borate,
(44) 1-benzyl-2-(methyamino)ethyl bis(3-chloro-4-methylphenyl)borate,
(45) 1-phenyl-2-aminoethyl bis(3-chloro-4-methylphenyl)borate,
(46) 1-(4-chlorophenoxymethyl)-2-(methylamino)ethyl bis(3-chloro-4-methylphenyl)borate,
(47) 1-phenyl-2-(1-(ethoxycarbonyl)-piperidine-4-ylamino)ethyl bis(3-chloro-4-methylphenyl)borate,
(48) 1-(methylaminomethyl)nonyl bis(3-chloro-4-methylphenyl)borate,
(49) 3-phenyl-1-(2-pyridyl)propyl bis(3-chloro-4-methylphenyl)borate,
(50) cis-3-phenyl-1-(2-pyridyl)-2-propenyl bis(3-chloro-4-methylphenyl)borate,
(51) 1-(5-methylimidazol-4-yl)-1-phenylmethyl bis(3-chloro-4-methylphenyl)borate,
(52) 1-(2-imidazolyl)-1-phenylmethyl bis(3-chloro-4-methylphenyl)borate,
(53) 1-(2-pyridyl)ethyl bis(3-chloro-4-methylphenyl)borate,
(54) 1-(2-pyridyl)-2-propenyl bis(3-chloro-4-methylphenyl)borate,
(55) 1-methyl-1-(2-pyridyl)ethyl bis(3-chloro-4-methylphenyl)borate,
(56) 1-phenyl-1-(2-aminophenyl)methyl bis(3-chloro-4-methylphenyl)borate,
(57) (1S,2R)-1,2-diphenyl-2-aminoethyl bis(3-chloro-4-methylphenyl)borate,
(58) (1R,2S)-1,2-diphenyl-2-aminoethyl bis(3-chloro-4-methylphenyl)borate,
(59) 1-phenyl-1-(pyrazin-2-yl)methyl bis(3-chloro-4-methylphenyl)borate,
(60) 1-(dimethylaminomethyl)-2-dimethylaminoethyl bis(3-chloro-4-methylphenyl)borate,
(61) 1-(pyrazol-3-yl)-1-phenylmethyl bis(3-chloro-4-methylphenyl)borate,
(62) 1-(4-trifluoromethylphenyl)-1-(2-pyridyl)methyl bis(3-chloro-4-methylphenyl)borate,
(63) 1-(4-acetylamino)phenyl-1-(2-pyridyl)methyl bis(3-chloro-4-methylphenyl)borate,
(64) 2-aminoethyl bis(4-chloro-3-trifluoromethylphenyl)borate,
(65) 1-(3-chloropyridin-2-yl)-1-phenylmethyl bis(3-chloro-4-methylphenyl)borate,
(66) 2-aminoethyl bis(3,5-di(trifluoromethyl)phenyl)borate,
(67) 2-aminoethyl bis(3,4,5-trifluorophenyl)borate,
(68) 2-aminoethyl bis(2,3,4-trifluorophenyl)borate,
(69) 2-aminoethyl bis(3-chloro-4-(1,1-dimethylethyl)phenyl)borate,
(70) 1-(4-nitropyridin-2-yl)-1-phenylmethyl bis(3-chloro-4-methylphenyl)borate,
(71) 1-(4-bromopyridin-2-yl)-1-phenylmethyl bis(3-chloro-4-methylphenyl)borate,
(72) 5,6,7,8-tetrahydroquinolin-8-yl bis(3-chloro-4-methylphenyl)borate,
(73) 2-aminoethyl (4-chlorophenyl)(4-chloro-2-methoxyphenyl)borate,
(74) 2-aminoethyl (4-chlorophenyl)(1-naphthyl)borate,
(75) 2-aminoethyl (4-chlorophenyl)(1,1'-biphenyl-4-yl)borate,
(76) 2-aminoethyl (4-chlorophenyl)(3-chloro-4-phenoxymethyl)phenylborate,
(77) 2-aminoethyl (4-chlorophenyl)(benzothiazol-2-yl)borate,
(78) 2-aminoethyl (4-chlorophenyl)(4-methylnaphthyl-1-yl)borate,
(79) 2-aminoethyl (3-phenylpropyl)phenylborate,
(80) 2-aminoethyl (3,3-diphenylpropyl)phenylborate,
(81) 2-aminoethyl (2-phenoxyphenyl)phenylborate,
(82) 2-aminoethyl (4-vinylphenyl)(3,4-dichlorophenyl)borate,
(83) 2-aminoethyl (4-bromophenyl)(4-chlorophenyl)borate,
(84) 2-aminoethyl (4-chlorophenyl)(4-(1,1'-dimethylethyl)phenyl)borate,
(85) 2-aminoethyl (4-chlorophenyl)(4-iodophenyl)borate,
(86) 2-aminoethyl (4-chlorophenyl)(1,1'-biphenyl-2-yl)borate,
(87) 2-aminoethyl (3-pyridyl)phenylborate,
(88) 2-aminoethyl (3-pyridyl)(4-chlorophenyl)borate,
(89) bis[2-[(2-aminoethoxy)phenylboryl]benzyl]ether,
(90) bis[4-[(2-aminoethoxy)phenylboryl]benzyl]ether,
(91) [4-[(2-aminoethoxy)phenylboryl]benzyl][2-[4-[(2-aminoethoxy)phenylboryl]phenyl]ethyl]ether,
(92) [2-[(2-aminoethoxy)phenylboryl]benzyl][2-[4-[(2-aminoethoxy)phenylboryl]phenyl]ethyl]ether,
(93) 10H-phenoxaborin-10-ol,
(94) 1,3-bis(4-chlorophenyl)-1,3-dihydro-2,1-benzoxaborole,
(95) 2,2-dimethyl-2-aminoethyl bisphenylborate,
(96) 2-pyridylmethyl bisphenylborate,
(97) 2-aminoethyl bis(2-methylphenyl)borate,
(98) 2-aminoethyl bis(4-chlorophenyl)borate,
(99) (2-methoxyphenyl)boronic acid,
(100) (4-trifluoromethylphenyl)boronic acid,
(101) (2-phenylthiophenyl)boronic acid,
(102) 2-aminoethyl bis(1-naphthyl)borate,
(103) 2-aminoethyl bis(4-fluorophenyl)borate,
(104) 2-aminoethyl bis(3-methylphenyl)borate,
(105) 2-aminoethyl bis(1,1'-biphenyl-4-yl)borate,
(106) 2-aminoethyl bis(3-chlorophenyl)borate,
(107) 2-aminoethyl bis(4-methylthiophenyl)borate,
(108) 2-aminoethyl bis(3-trifluoromethylphenyl)borate,
(109) 2-aminoethyl (4-chlorophenyl)phenylborate,
(110) 2-aminoethyl bis(3,4-dichlorophenyl)borate,
(111) bis(2-aminoethyl)p-phenylenebis(phenylborate),
(112) tetraphenyl diboroxide or nontoxic salts thereof.

The compounds are preferably
(1) (3-chloro-4-methylphenyl)(4-4-benzyloxymethylphenyl)borate,
(2) (2-diethylaminocarbonylphenyl)phenylborate,
(3) (4-chlorophenyl)(4-benzyloxymethylphenyl)borate,
(4) (4-chlorophenyl)(4-(4-methoxybenzyloxymethyl)phenyl)borate,
(5) (4-chlorophenyl)[4-(1,2,3,4-tetrahydronaphtho-1-yloxymethyl)phenyl]borate,
(6) (4-chlorophenyl)(4-(2-phenylethoxy)methylphenyl)borate, (7) (4-chlorophenyl)[4-(cyclohexyloxymethyl)phenyl]borate,
(8) (4-chlorophenyl)[4-(butoxymethyl)phenyl]borate,
(9) (1,1'-biphenyl-4-yl)[4-(benzyloxymethyl)phenyl]borate,
(10) (4-chlorophenyl)[3-(benzyloxymethyl)phenyl]borate,
(11) (3,5-dichlorophenyl)(4-benzyloxymethylphenyl)borate,
(12) (4-bromophenyl)(4-(benzyloxymethyl)phenyl)borate,
(13) (4-chlorophenyl)[4-(2-(phenylaminocarbonyloxy)ethyl)phenyl]borate,
(14) (4-chlorophenyl)[4-(2-(methoxycarbonyloxy)ethyl)phenyl]borate,
(15) (4-chlorophenyl)[4-(2-((2-methyl-4-nitrophenyl)aminocarbonyloxy)ethyl)phenyl]borate,
(16) (4-chlorophenyl)[4-(2-((3,5-di(methoxycarbonyl)phenyl)aminocarbonyloxy)ethyl)phenyl]borate,
(17) (4-chlorophenyl)[4-(2-(1-ethoxycarbonyl-2-methylpropylcarbamoyloxy)ethyl)phenyl]borate,
(18) bis[2-(hydroxyphenylboryl)benzyl]ether,
(19) 1,4-bis(4-(hydroxyphenylboryl)phenoxy)butane,
(20) bis[4-(hydroxyphenylboryl)benzyl]ether,
(21) bis(3-chloro-4-methylphenyl)borate,
(22) bis[4-(2-(methoxycarbonyl)vinyl)phenyl]borate,
(23) 2-cyclohexylaminoethyl bis(3-chloro-4-methylphenyl)borate,
(24) 2-aminoethyl bis(4-trifluoromethylphenyl)borate,
(25) 2-aminoethyl dicyclopentylborate,
(26) 2-aminoethyl bis(4-chloro-2-methylphenyl)borate,
(27) 2-aminoethyl bis(4-dimethylaminosulfonylphenyl)borate,
(28) 2-aminoethyl bis(2-naphthyl)borate,
(29) 2-aminoethyl bis(4-chloro-3-methylphenyl)borate,
(30) 2-aminoethyl bis(3-chloro-4-methylphenyl)borate,
(31) 2-aminoethyl bis(3,5-dichlorophenyl)borate,
(32) 2-pyridylmethyl bis(3-chloro-4-methylphenyl)borate,
(33) 2-dimethylaminoethyl bis(3-chloro-4-methylphenyl)borate,
(34) 1-methyl-2-aminoethyl bis(3-chloro-4-methylphenyl)borate,
(35) 2-(phenylamino)ethyl bis(3-chloro-4-methylphenyl)borate,
(36) 2-amino-4-guanidino-1-oxobutyl bis(4-chlorophenyl)borate,
(37) 2-(benzylamino)ethyl bis(3-chloro-4-methylphenyl)borate,
(38) 3-(benzyl-1,2,3-triazol-4-yl)methyl bis(3-chloro-4-methylphenyl)borate,
(39) 2-phenyl-2-aminoethyl bis(3-chloro-4-methylphenyl)borate,
(40) 2-(piperazin-1-yl)ethyl bis(3-chloro-4-methylphenyl)borate,
(41) 2-(butylamino)ethyl bis(3-chloro-4-methylphenyl)borate,
(42) 1-phenyl-1-(2-pyridyl)methyl bis(3-chloro-4-methylphenyl)borate,
(43) 2-amino-2-(methoxycarbonyl)ethyl bis(4-chlorophenyl)borate,
(44) 1-benzyl-2-(methyamino)ethyl bis(3-chloro-4-methylphenyl)borate,
(45) 1-phenyl-2-aminoethyl bis(3-chloro-4-methylphenyl)borate,
(46) 1-(4-chlorophenoxymethyl)-2-(methylamino)ethyl bis(3-chloro-4-methylphenyl)borate,
(47) 1-phenyl-2-(1-(ethoxycarbonyl)-piperidine-4-ylamino)ethyl bis(3-chloro-4-methylphenyl)borate,
(48) 1-(methylaminomethyl)nonyl bis(3-chloro-4-methylphenyl)borate,
(49) 3-phenyl-1-(2-pyridyl)propyl bis(3-chloro-4-methylphenyl)borate,
(50) cis-3-phenyl-1-(2-pyridyl)-2-propenyl bis(3-chloro-4-methylphenyl)borate,
(51) 1-(5-methylimidazol-4-yl)-1-phenylmethyl bis(3-chloro-4-methylphenyl)borate,
(52) 1-(2-imidazolyl)-1-phenylmethyl bis(3-chloro-4-methylphenyl)borate,
(53) 1-(2-pyridyl)ethyl bis(3-chloro-4-methylphenyl)borate,
(54) 1-(2-pyridyl)-2-propenyl bis(3-chloro-4-methylphenyl)borate,
(55) 1-methyl-1-(2-pyridyl)ethyl bis(3-chloro-4-methylphenyl)borate,
(56) 1-phenyl-1-(2-aminophenyl)methyl bis(3-chloro-4-methylphenyl)borate,
(57) (1S,2R)-1,2-diphenyl-2-aminoethyl bis(3-chloro-4-methylphenyl)borate,
(58) (1R,2S)-1,2-diphenyl-2-aminoethyl bis(3-chloro-4-methylphenyl)borate,
(59) 1-phenyl-1-(pyrazin-2-yl)methyl bis(3-chloro-4-methylphenyl)borate,
(60) 1-(dimethylaminomethyl)-2-dimethylaminoethyl bis(3-chloro-4-methylphenyl)borate,
(61) 1-(pyrazol-3-yl)-1-phenylmethyl bis(3-chloro-4-methylphenyl)borate,
(62) 1-(4-trifluoromethylphenyl)-1-(2-pyridyl)methyl bis(3-chloro-4-methylphenyl)borate,
(63) 1-(4-acetylamino)phenyl-1-(2-pyridyl)methyl bis(3-chloro-4-methylphenyl)borate,
(64) 2-aminoethyl bis(4-chloro-3-trifluoromethylphenyl)borate,
(65) 1-(3-chloropyridin-2-yl)-1-phenylmethyl bis(3-chloro-4-methylphenyl)borate,
(66) 2-aminoethyl bis(3,5-di(trifluoromethyl)phenyl)borate,
(67) 2-aminoethyl bis(3,4,5-trifluorophenyl)borate,
(68) 2-aminoethyl bis(2,3,4-trifluorophenyl)borate,
(69) 2-aminoethyl bis(3-chloro-4-(1,1-dimethylethyl)phenyl)borate,
(70) 1-(4-nitropyridin-2-yl)-1-phenylmethyl bis(3-chloro-4-methylphenyl)borate,
(71) 1-(4-bromopyridin-2-yl)-1-phenylmethyl bis(3-chloro-4-methylphenyl)borate,
(72) 5,6,7,8-tetrahydroquinolin-8-yl bis(3-chloro-4-methylphenyl)borate,
(73) 2-aminoethyl (4-chlorophenyl)(4-chloro-2-methoxyphenyl)borate,
(74) 2-aminoethyl (4-chlorophenyl)(1-naphthyl)borate,
(75) 2-aminoethyl (4-chlorophenyl)(1,1'-biphenyl-4-yl)borate,
(76) 2-aminoethyl (4-chlorophenyl)(3-chloro-4-phenoxymethyl)phenylborate,
(77) 2-aminoethyl (4-chlorophenyl)(benzothiazol-2-yl)borate,
(78) 2-aminoethyl (4-chlorophenyl)(4-methylnaphthyl-1-yl)borate,
(79) 2-aminoethyl (3-phenylpropyl)phenylborate,
(80) 2-aminoethyl (3,3-diphenylpropyl)phenylborate,
(81) 2-aminoethyl (2-phenoxyphenyl)phenylborate,
(82) 2-aminoethyl (4-vinylphenyl)(3,4-dichlorophenyl)borate,
(83) 2-aminoethyl (4-bromophenyl)(4-chlorophenyl)borate,
(84) 2-aminoethyl (4-chlorophenyl)(4-(1,1'-dimethylethyl)phenyl)borate,
(85) 2-aminoethyl (4-chlorophenyl)(4-iodophenyl)borate,
(86) 2-aminoethyl (4-chlorophenyl)(1,1'-biphenyl-2-yl)borate,
(87) 2-aminoethyl (3-pyridyl)phenylborate,

(88) 2-aminoethyl (3-pyridyl)(4-chlorophenyl)borate,
(89) bis[2-[(2-aminoethoxy)phenylboryl]benzyl]ether,
(90) bis[4-[(2-aminoethoxy)phenylboryl]benzyl]ether,
(91) [4-[(2-aminoethoxy)phenylboryl]benzyl][2-[4-[(2-aminoethoxy)phenylboryl]phenyl]ethyl]ether,
(92) [2-[(2-aminoethoxy)phenylboryl]benzyl][2-[4-[(2-aminoethoxy)phenylboryl]phenyl]ethyl]ether,
(93) 10H-phenoxaborin-10-ol,
(94) 1,3-bis(4-chlorophenyl)-1,3-dihydro-2,1-benzoxaborole or nontoxic salts thereof.

Salts

The compounds of formula (I) of the present invention may be converted into corresponding non-toxic salts by conventional methods. Non-toxic salts in the present specification include alkali metal salts, alkaline earth metal salts, amine salts, ammonium salts, acid-addition salts, hydrates, etc.

Non-toxic and water-soluble salts are preferable. Appropriate non-toxic salts include salts of alkali metals (potassium, sodium, etc.), salts of alkaline-earth metals (calcium, magnesium, etc.), ammonium salts and salts of pharmaceutically-acceptable organic amines (tetramethyl ammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.), and are preferably salts of alkaline-earth metals.

Non-toxic, water-soluble acid-addition salts are preferable. Appropriate acid-addition salts are inorganic salts such as hydrochloride, hydrobromide, sulfate, phosphate, nitrate, or organic salts such as acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate, gluconate.

The compounds of formula (I) of the present invention or a salt thereof may be converted into hydrate by a conventional method.

Process for the Preparation of the Compounds of the Present Invention

The compound represented by formula (1) used in the present invention may be produced by the methods described below or in Examples. That is, the compound represented by formula (I) may be prepared by subjecting a compound of formula (I-1)

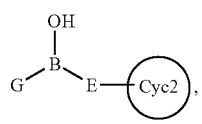

(I-1)

wherein all the symbols have the same meanings as above, to reaction with a compound represented by formula (II)

HO—(CH$_2$)$_n$—NR$^2$R$^3$    (II), wherein all the symbols have the same meanings as above, or to reaction with a compound represented by formula (III)

HO—Z—Cyc3    (III), wherein Z represents C1–6 alkylene or C2–6 alkenylene and Cyc3 represents mono-cyclic C5–6 carboring which may be substituted with 1 to 5 R$^7$, or to reaction with a compound represented by formula (IV)

HO—Z—Cyc4    (IV), wherein Cyc4 represents mono-cyclic 5–6 membered heteroring which may be substituted with 1 to 5 R$^7$ and other symbols have the same meanings as above, or to reaction with a compound represented by formula (V)

(V)

wherein all the symbols have the same meanings as above, or to reaction with a compound represented by formula (VI)

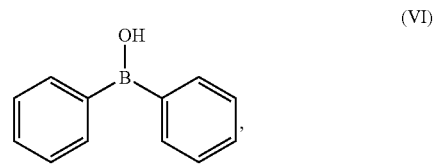

(VI)

wherein all the symbols have the same meanings as above.

These reactions are known, and the compound may be prepared by carrying out the reaction in organic solvents (ethanol, toluene, etc.) at a temperature of 0 to 50° C.

The compound represented by formula (I-1) maybe produced by the methods described in the following (a) to (c).

(a) Among the compounds of formula (I-1), the compound wherein G is Cyc1, Cyc1 and Cyc2 are the same group, and E is a single bond, i.e., the compound of formula (I-1a)

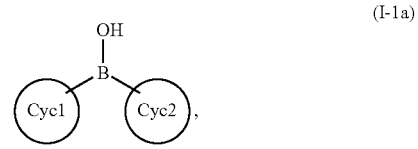

(I-1a)

wherein all the symbols have the same meanings above, however, Cyc1 and Cyc2 represent the same group, may be prepared by the method indicated by the reaction formula (a).

Reaction Formula (a)

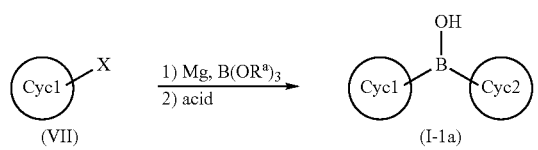

In the reaction formula (a), X is a halogen atom, R$^a$ is methyl or isopropyl and the other symbols have the same meanings above.

This reaction is known, and the compound may be prepared by subjecting to reaction the Grignard reagent prepared from magnesium and a compound represented by formula (VII) with a boron compound (trimethyl borate, triisopropyl borate, etc.) in organic solvents (such as tetrahydrofuran) at a temperature of −78 to 50° C. and then to acid (such as hydrochloric acid) treatment.

(b) Among the compounds of formula (I-1), the compound wherein G is Cyc1, (i) Cyc1 and Cyc2 are different rings or rings containing different substituent groups; and E is a single bond, or C1–4 alkyl substitued with phenyl or not substituted; or (ii) Cyc1 and Cyc2 are the same group and E is C1–4 alkyl substitued with phenyl or not substituted; i.e., the compound of formula (I-1b)

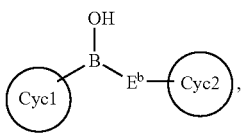

(I-1b)

wherein $E^b$ is (i) a single bond or C1–4 alkyl substitued with phenyl or not substituted when Cyc1 and Cyc2 are different rings or rings containing different substituent groups, (ii) C1–4 alkyl substitued with phenyl or not substituted when Cyc1 and Cyc2 are the same group, and the other symbols have the same meanings as above, may be prepared by the method indicated by the reaction formula (b).

Reaction Formula (b)

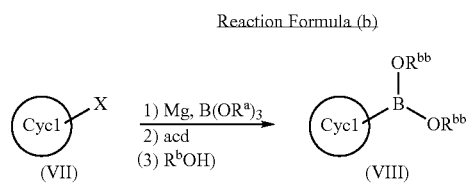

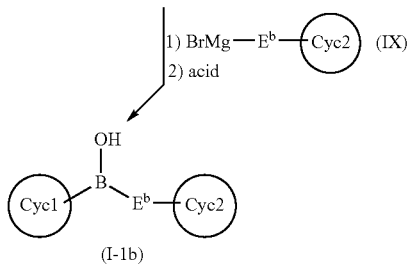

In the reaction formula (b), $R^b$ is methyl or ethyl, $R^{bb}$ is a hydrogen atom, methyl or ethyl and the other symbols have the same meanings above.

This reaction is known, and the compound may be prepared by subjecting to reaction a compound represented by formula (VIII), which is prepared by subjecting the Grignard reagent prepared from magnesium and a compound represented by formula (VII) with a boron compound (trimethyl borate, triisopropyl borate, etc.) in organic solvents (such as tetrahydrofuran) at a temperature of −78 to 50° C., with a compound represented by formula (IX) in organic solvents (such as tetrahydrofuran) at a temperature of −78 to 50° C. and then to acid (such as hydrochloric acid) treatment.

(c) Among the compounds of formula (I-1), the compound wherein G is Cyc1, E is a single bond and the substituent group of Cyc1 is

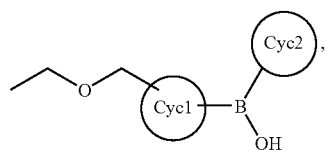

i.e., the compound represented by formula (I-1c)

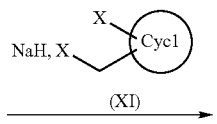

(I-1c)

may be prepared, for example, by the method indicated by the reaction formula (c).

Reaction Formula (c)

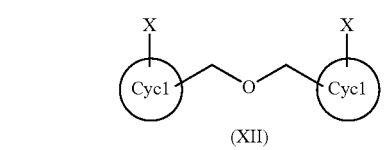

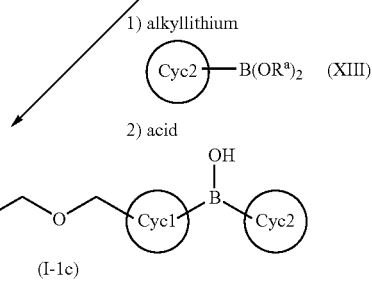

(I-1c)

In the reaction formula (c), all the symbols have the same meanings as above.

This reaction is known, and the compound may be prepared by subjecting to reaction a compound represented by formula (XII), which is prepared by subjecting a compound represented by formula (X) with a compound represented by formula (XI) in organic solvents (such as tetrahydrofuran) at a temperature of 0 to 50° C., with alkyllithium reagent (such as n-butyllithium) in organic solvents (such as tetrahydrofuran) at a temperature of −78° C. and then to acid (such as hydrochloric acid) treatment.

The starting materials and each reagent of the present invention are known per se or may be prepared by known methods.

In each reaction of the present specification, reaction products may be purified by conventional techniques. For example, purification may be carried out by distillation under atmospheric or reduced pressure, by high performance liquid chromatography, thin layer chromatography or column chromatography using silica gel or magnesium silicate, by washing or by recrystallization, etc. Purification may be carried out after each reaction or after a series of reactions.

Pharmacological Activity

It has been proved that the compound of the present invention has an activity to decrease the intracellular calcium concentration, for example, by the following experiments.

(1) Inhibitory Activity Against Capacitative Calcium Entry

Method of the Experiment

Fura-2 acetoxymethylester was introduced to the cell strain deficient of $IP_3$ receptors produced from the cultivated cell strain DT40 from chickens. The intracellular calcium concentration was measured by the measurement of the fluorescence of 510 nm obtained at 2-wavelength excitation of 340 nm and 380 nm, and its fluorescence ratio F=340/380.

Intracellular calcium store was depleted by activating tapsigalguine (inhibitor of the endoplasmic reticulum calcium pump) without the presence of the calcium ion in the extracellular fluid. Calcium chloride solution of the ultimate concentration of 2 mM was added to the extracellular fluid, and the influence of each compound to the increase rate of the intracellular calcium concentration was estimated at the point of adding the solution to thereby determine the value of $IC_{50}$.

2-aminoethyl diphenylborinate was used as a comparative compound.

The results are shown in Table 1.

TABLE 1

| Compound No. | $IC_{50}$ (µM) |
|---|---|
| (25) | 0.66 |
| (53) | 0.63 |
| (60) | 0.35 |
| (62) | 0.13 |
| (90) | 0.059 |
| Comparative Compound | 5.0 |

(2) Inhibitory Activity Against Calcium Release by $IP_3$

Method of the Experiment

According to the methods by S. Nakade (Biochem. J., 277, 125–131(1991)) and the like, cerebellum of mouse was taken out, homogenated and centrifuged (12,000 g, for 15 minutes). Furthermore, the supernatant was centrifuged (105,000 g, for 60 minutes). 2 µM of fura2, 1.25 mM of ATP, 10V/ml of creatine kinase, 10 mM of creatine phosphate and 2.5 µg/ml of oligomycin were added to the sediment, and calcium was made endocytosed in the microsome. Then $IP_3$ was added thereto, and the released calcium was measured by the measurement of the fluorescence of 500 nm obtained at 2-wavelength excitation of 340 nm and 380 nm, and the fluorescence ratio F=340/380. Defining the calcium released with 30 nM of $IP_3$ as 100%, the ratio of the calcium released in the presence of each subject compound was determined to thereby calculate the $IC_{50}$ value.

2-aminoethyl diphenylborinate was used as a comparative compound.

The results are shown in Table 2.

TABLE 2

| Compound No. | $IC_{50}$ (µM) |
|---|---|
| (3) | 3 |
| (30) | 2.6 |
| (47) | 3.8 |
| (53) | 3.6 |
| (84) | 4.5 |
| (90) | 6 |
| Comparative Compound | 20 |

From the above-mentioned results, it has been proved that the compound of the present invention has an activity to effectively control the increase of the intracellular calcium concentration, by controlling the endogenous calcium release orcapacitative calciumentry. Compound (53) and Compound (90) have been proved that they have an activity to effectively control the increase of the intracellular calcium concentration, by controlling the endogenous calcium release or capacitative calcium entry. Moreover, the activity of the compounds represented by formula (1), not only of those having a structure of $R^1$ group different from that of the comparative compounds but also of those having a similar structure, was much more stronger compared to that of the comparative compounds.

Toxicity

The toxicity of the compounds of the present invention is very low and therefore it was confirmed that the compounds are safe for pharmaceutical use.

Industrial Applicability

Application to Pharmaceuticals

The compound of the present invention has an action inhibiting the increase of the intracellular calcium concentration, and therefore it is deemed to be useful as an agent for the prophylaxis and/or treatment of platelet aggregation, immune deficiency diseases, allergosis, ischemic diseases in hearts and brains, bronchial asthma, hypertension, cerebrovascular spasm, various renal diseases, pancreatitis or Alzheimer's disease.

The compound of the present invention or nontoxic salts thereof may be administered as a concomitant medication in combination of other medical agents for the purposes:

1) to supplement and/or enhance the effects of the compound on the prophylaxis and/or treatment,
2) to improve dynamic forces and absorption of the compound, to reduce of doses of the compound, and/or
3) to alleviate the side-effects of the compound.

The concomitant medication of the compound of the present invention and other agents may be administered as a combination drug dispensing both compositions in one preparation, or may be administered in separate preparations. In the case that the concomitant is administered in separate preparations, the administration includes simultaneous administration and time-interval administration. In time-interval administration, the compound of the present invention may be administered prior to the other agent or vice versa, and the each administration method may be the same of different.

The diseases for which the above concomitant is used effectively for the prophylaxis and/or treatment are not specifically limited but for any disease for which the effects of the compound on the prophylaxis and/or treatment is supplemented and/or enhanced.

The weight ratio of the compound of the present invention and other agents is not specifically limited.

The other agents may be administered in a combination of arbitrary two or more agents.

The other agents, which supplement and/or enhance the effects of the compound of the present invention for the prophylaxis and/or treatment, are not limited to those found to date based on the above mechanism but those to be found hereafter are included.

For the purpose described above, the compounds of formula (I), of the present invention, non-toxic salts thereof, acid addition salts thereof or hydrates thereof may normally be administered systemically or locally, usually by oral or parenteral administration.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, once or up to several times per day, and from 0.1 mg to 100 mg, by parenteral administration (preferably intravenous administration), once or up to several times per day, or continuous administration for from 1 to 24 hours per day from vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules.

In such solid compositions, one or more of the active compound(s) maybe used as a dosage form, as is normal practice, to admix with excipient (e.g. lactose, mannitol, glucose, microcrystalline cellulose, starch), combining agents (hydroxypropyl cellulose, polyvinyl pyrrolidone or magnesiummetasilicate aluminate), disintegrating agents (e.g. cellulose calcium glycolate), lubricating agents (e.g. magnesium stearate), stabilizing agents, agents to assist dissolution (e.g. glutamic acid or asparatic acid) and the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, one or more of the active compound(s) are dissolved, suspended or emulsified in diluent commonly used (e.g. purified water, ethanol or mixture thereof). Furthermore, such liquid compositions may also comprise wetting agents or suspending agents, emulsifying agents, sweetening agents, flavouring agents, perfuming agents, preserving agents, buffer agent, etc.

Injections for parenteral administration include solutions, suspensions, emulsions and solids which are dissolved or suspended to use at a time to use. One or more of the active compound(s) in injections are dissolved, suspended and emulsified in a solvent. The solvents are, for example, distilled water for injection, physiological salt solution, vegetable oil, propylene glycol, polyethylene glycol, alcohol such as ethanol or mixture thereof. Moreover the injections may also include stabilizing agents, agents to assist dissolution (e.g. glutamic acid, aspartic acid or POLYSORBATE80 (registered trade mark)), suspending agents, emulsifyingagents, soothingagents, buffer agents, preserving agents, etc. They are sterilized in the last process or manufactured and prepared by sterile procedure. They may also be manufactured in the form of sterile solid compositions such as freeze-dried one and they may be sterilized or dissolved to use in sterile distilled water for injection or some other solvents immediately before use.

Other compositions for parenteral administration include liquids for external use, and ointment, endermic liniments, inhale, spray, suppositories for rectal administration and pessaries for vaginal administration which comprise one or more of the active compound(s) and are prescribed by methods known per se.

Spray compositions may comprise additional substances other than diluents: e.g. stabilizing agents (e.g. sodium sulfite hydride), isotonic buffers (e.g. sodium chloride, sodium citrate or citric acid). For preparation of such spray compositions, for example, the method described in the U.S. Pat. No. 2,868,691 or No. 3,095,355 may be used.

BEST MODE FOR CARRYING OUT THE INVENTION

The following Reference Examples and Examples illustrate the present invention, but do not limit the present invention.

The solvents in the parentheses show the eluting or developing solvents and the ratios of the solvents used are by volume in chromatographic separations or TLC.

The solvents in the parentheses in NMR show the solvents used in measurement.

REFERENCE EXAMPLE 1

(4-benzyloxymethylphenyl)boronic acid

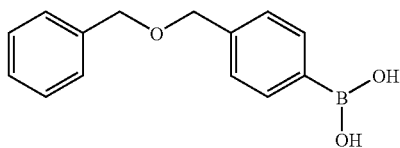

After ignition drying of magnesium piece (357 mg) in vacuo and purging with argon, anhydrous tetrahydrofuran (THF; 20 ml) was added thereto and solution of 1-benzyloxymethyl-4-bromobenzen (3.3 g) in THF (30 ml) was delivered by drops over one hour. The reaction mixture was added to solution of trimethyl borate (1.7 ml) in THF (20 ml) cooled to −78° C. and stirred for four hours at room temperature. 1N hydrochloric acid was added to the reaction mixture and the water layer was extracted with ethyl acetate. The organic layer was dried with anhydrous sodium sulfate and concentrated to obtain the title compound (1.8 g) having the following physical data.

TLC: Rf 0.55 (hexane:ethyl acetate=1:2)

EXAMPLE 1

(3-chloro-4-methylphenyl)(4-benzyloxymethylphenyl)borate

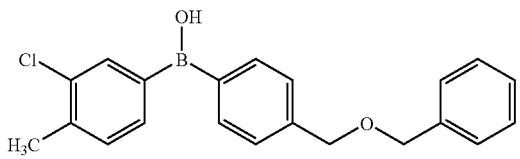

Solution of the compound produced in Reference Example 1 (410 mg) in THF (4 ml) was slowly added to solution of Grignard agent (3-chloro-4-methylphenylmagnesium bromide) in THF (1.3 ml). The mixture was stirred for 30 minutes and left standing until cooled down to room temperature. 1N hydrochloric acid was added to the reaction mixture and the water layer was extracted with isopropyl ether. The organic layer was dried with anhydrous magnesium sulfate and concentrated. The residue was purified by column chromatography to obtain the title compound (127 mg) having the following physical data.

TLC: Rf 0.35 (hexane:ethyl acetate=2:1) NMR (CDCl$_3$): δ7.76 (3H, d, J=7.0 Hz), 7.59 (1H, d, J=7.5 Hz), 7.50–7.20 (9H, m), 5.88 (1H, bs), 4.63 (2H, s), 4.60 (2H, s), 2.44 (3H, s)

EXAMPLES 1(1) to 1(16)

The same operations in Reference Example 1 to Example 1 were performed using corresponding compounds to obtain the following compounds.

EXAMPLE 1(1)

(2-diethylaminocarbonylphenyl)phenyl borate

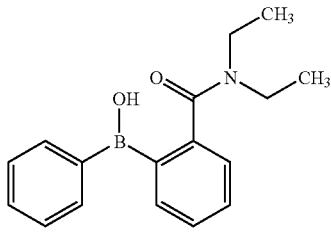

TLC: Rf 0.54 (hexane:ethyl acetate=3:1) NMR (CDCl$_3$): δ7.77 (1H, d, J=7.0 Hz), 7.74 (1H, d, J=7.0 Hz), 7.60–7.25 (7H, m), 5.72 (1H, bs), 3.42 (2H, q, J=7.5 Hz), 3.24 (2H, q, J=7.5 Hz), 1.12 (3H, t, J=7.5 Hz), 1.08 (3H, t, J=7.5 Hz).

EXAMPLES 1(2)

(4-chlorophenyl)(4-benzyloxymethylphenyl)borate

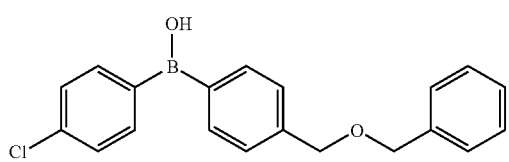

TLC: Rf 0.38 (hexane:ethyl acetate=2:1) NMR (CDCl$_3$): δ7.76 (4H, d, J=7.5 Hz), 7.52–7.22 (9H, m), 6.20–5.70 (1H, bs), 4.62 (2H, s), 4.61 (2H, s).

EXAMPLE 1(3)

(4-chlorophenyl)(4-(4-methoxybenzyloxymethyl)phenyl)borate

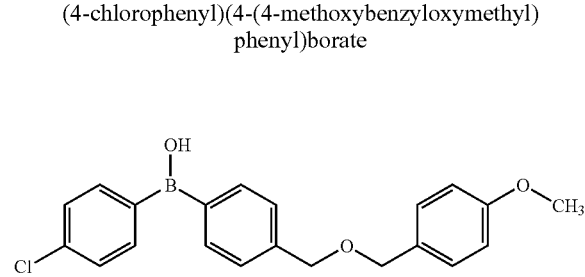

TLC: Rf 0.54 (acetonitrile:water=3:1, reverse phase); NMR(CDCl$_3$): δ7.74 (2H, d, J=7.5 Hz), 7.68 (2H, d, J=8.0 Hz), 7.42 (2H, d, J=5.5 Hz), 7.40 (2H, d, J=5.5 Hz), 7.28 (2H, d, J=7.5 Hz), 6.90 (2H, d, J=8.0 Hz), 6.35–6.04 (1H, bs), 4.59 (2H, s), 4.53 (2H, s), 3.80 (3H, s).

EXAMPLE 1(4)

(4-chlorophenyl)[4-(1,2,3,4-tetrahydronaphto-1-yloxymethyl)phenyl]borate

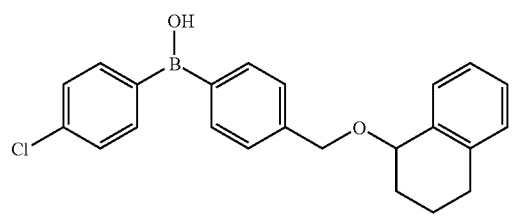

TLC: Rf 0.43 (hexane:ethyl acetate=2:1); NMR(CDCl$_3$): δ7.75 (4H, d, J=7.5 Hz), 7.56–7.28 (6H, m), 7.22–7.06 (2H, m), 5.88 (1H, bs), 4.75 (1H, d, J=13 Hz), 4.62 (1H, d, J=13 Hz), 4.55 (1H, t, J=4.5 Hz), 2.98–2.65 (2H, m), 2.18–1.95 (3H, m), 1.95–1.72 (1H, m).

EXAMPLE 1(5)

(4-chlorophenyl)[4-(2-phenylethoxy)methylphenyl]borate

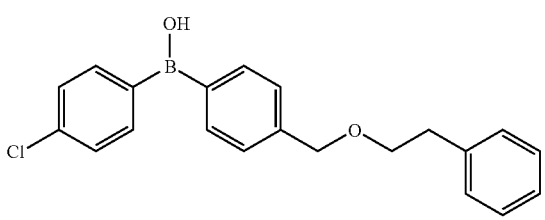

TLC: Rf 0.35 (hexane:ethyl acetate=3:1); NMR (CDCl$_3$): δ7.74 (2H, d, J=6.0 Hz), 7.68 (2H, d, J=6.0 Hz), 7.42 (2H, d, J=8.0 Hz), 7.38 (2H, d, J=8.0 Hz), 7.28–7.14 (5H, m), 5.88 (1H, bs), 4.59 (2H, s), 3.72 (2H, t, J=7.0 Hz), 2.94 (2H, t, J=7.0 Hz).

EXAMPLE 1(6)

(4-chlorophenyl)[4-(cyclohexyloxymethyl)phenyl]borate

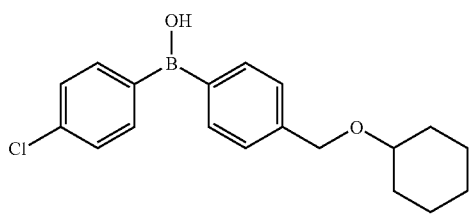

TLC: Rf 0.42 (hexane:ethyl acetate=3:1); NMR (CDCl$_3$): δ7.72 (4H, m), 7.42 (4H, m), 5.85 (1H, bs), 4.58 (2H, s), 3.38 (1H, m), 1.98 (2H, m), 1.78 (2H, m), 1.55 (2H, m), 1.44–1.12 (4H, m).

EXAMPLE 1(7)

(4-chlorophenyl)[4-(butoxymethyl)phenyl]borate

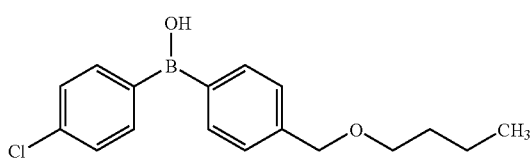

TLC: Rf 0.45 (hexane:ethyl acetate=3:1); NMR (CDCl$_3$): δ7.78 (2H, d, J=8.0 Hz), 7.75 (2H, d, J=7.5 Hz), 7.42 (4H, d, J=8.0 Hz), 7.88 (1H, bs), 4.56 (2H, s), 3.50 (2H, t, J=7.0 Hz), 1.60 (2H, m), 1.44 (2H, m), 0.94 (3H, t, J=7.0 Hz).

EXAMPLE 1(8)

(1,1'-biphenyl-4-yl)[4-(benzyloxymethyl)phenyl]borate

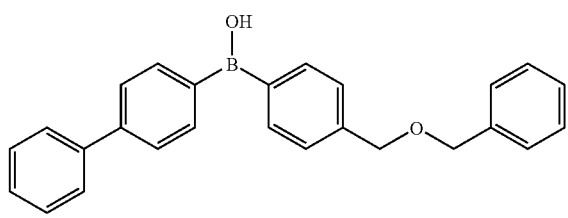

TLC: Rf 0.43 (hexane:ethyl acetate=2:1); NMR (CDCl$_3$): δ7.92 (2H, d, J=8.5 Hz), 7.82 (2H, d, J=7.5 Hz), 7.75–7.58 (4H, m), 7.55–7.28 (10H, m), 5.94 (1H, bs), 4.62 (2H, s), 4.60 (2H, s).

EXAMPLE 1(9)

(4-chlorophenyl)(3-(benzyloxymethyl)phenyl)borate

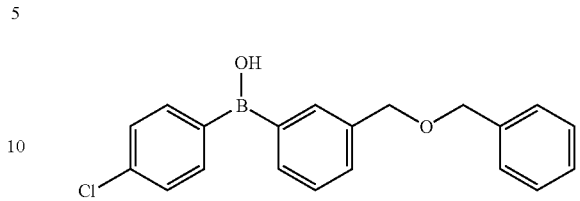

TLC: Rf 0.43 (hexane:ethyl acetate=2:1); NMR (CDCl$_3$): δ7.74 (3H, d, J=8.0 Hz), 7.66 (1H, d, J=5.5 Hz), 7.58–7.25 (9H, m), 5.95 (1H, bs), 4.58 (4H, m).

EXAMPLE 1(10)

(3,5-dichlorophenyl)(4-benzyloxymethylphenyl)borate

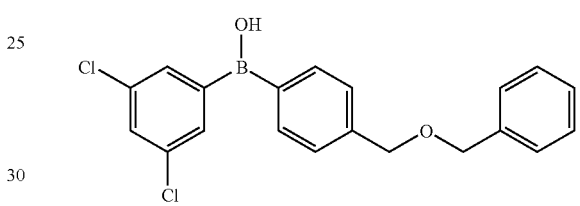

TLC: Rf 0.36 (hexane:ethyl acetate=2:1); NMR (CDCl$_3$): δ7.80 (2H, d, J=7.0 Hz), 7.45 (2H, d, J=7.0 Hz), 7.50–7.20 (8H, m), 5.84 (1H, bs), 4.81 (2H, s), 4.79 (2H, s).

EXAMPLE 1(11)

(4-bromophenyl)(4-(benzyloxymethyl)phenyl)borate

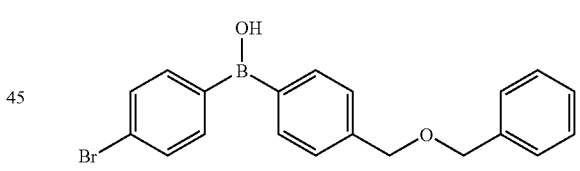

TLC: Rf 0.40 (hexane:ethyl acetate=3:2); NMR (CDCl$_3$): δ7.74 (2H, d, J=7.5 Hz), 7.68 (2H, d, J=8.0 Hz), 7.57 (2H, d, J=8.0 Hz), 7.45 (2H, d, J=7.5 Hz), 7.42–7.26 (5H, m), 5.95 (1H, bs), 4.60 (2H, s), 4.58 (2H, s).

EXAMPLE 1(12)

(4-chlorophenyl)[4-(2-(phenylaminocarbonyloxy)ethyl)phenyl]borate

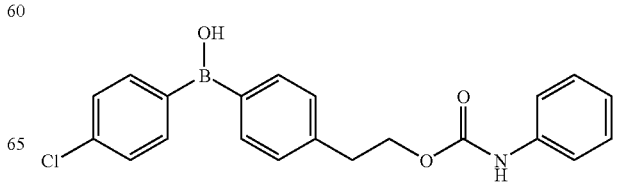

TLC: Rf 0.58 (chloroform:methanol=50:1); NMR (d$_6$-DMSO): δ9.88 (1H, s), 9.54 (1H, s), 7.69 (2H, d, J=8.0 Hz), 7.64 (2H, d, J=7.0 Hz), 7.46 (2H, d, J=8.0 Hz), 7.41 (2H, d, J=7.0 Hz), 7.33 (2H, d, J=7.0 Hz), 7.25 (2H, dd, J=7.0, 7.0 Hz), 6.95 (1H, dd, J=7.0, 7.0 Hz), 4.35 (2H, t, J=7.0 Hz), 3.02 (2H, t, J=7.0 Hz).

EXAMPLE 1(13)

(4-chlorophenyl)[4-(2-(methoxycarbonyloxy)ethyl)phenyl]borate

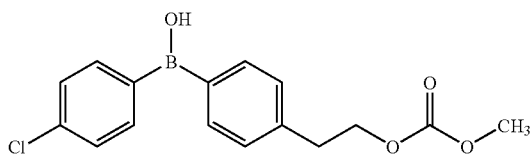

TLC: Rf 0.43 (hexane:ethyl acetate=2:1); NMR (CDCl$_3$): δ7.74 (2H, d, J=6.5 Hz), 7.70 (2H, d, J=9.5 Hz), 7.42 (2H, d, J=9.5 Hz), 7.28 (2H, d, J=6.5 Hz), 5.90 (1H, bs), 4.38 (2H, t, J=7.0 Hz), 3.78 (3H, s), 3.05 (2H, t, J=7.0 Hz).

EXAMPLE 1(14)

(4-chlorophenyl)[4-(2-((2-methyl-4-nitrophenyl)aminocarbonyloxy)ethyl)phenyl]borate

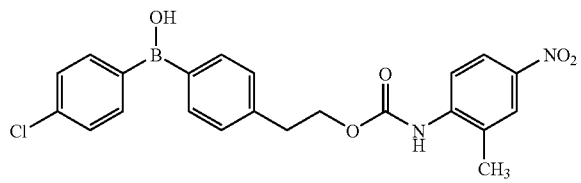

TLC: Rf 0.25 (hexane:ethyl acetate=2:1); NMR (CDCl$_3$+DMSO-d$_6$(5 drops)): δ9.18 (1H, bs), 8.05 (3H, s), 7.74 (2H, d, J=7.5 Hz), 7.73 (2H, d, J=7.5 Hz), 7.40–7.22 (4H, m), 4.47 (2H, t, J=7.0 Hz), 3.08 (2H, t, J=7.0 Hz), 2.35 (3H, s).

EXAMPLE 1(15)

(4-chlorophenyl)[4-(2-((3,5-di(methoxycarbonyl)phenyl)aminocarbonyloxy)ethyl)phenyl]borate

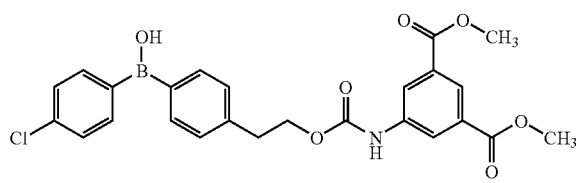

TLC: Rf 0.27 (hexane:ethyl acetate=1:1); NMR (d$_6$-DMSO+CDCl$_3$(10%)): δ10.5 (1H, s), 9.86 (1H, s), 8.38 (2H, s), 8.12 (1H, s), 7.72 (2H, d, J=8.0 Hz), 7.64 (2H, d, J=8.0 Hz), 7.41 (2H, d, J=8.0 Hz), 7.32 (2H, d, J=8.0 Hz), 4.38 (2H, t, J=6.0 Hz), 3.88 (6H, s), 3.02 (2H, t, J=6.0 Hz).

EXAMPLE 1(16)

(4-chlorophenyl)[4-(2-((1-ethoxycarbonyl-2-methylpropyl)carbamoyloxy)ethyl)phenyl]borate

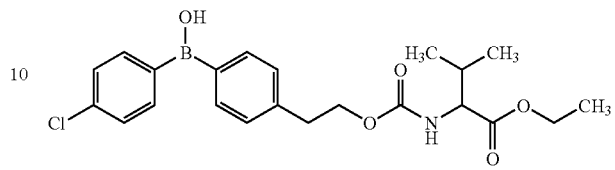

TLC: Rf 0.38 (hexane:ethyl acetate=1:1); NMR(CDCl$_3$): δ7.75 (2H, d, J=7.0 Hz), 7.65 (2H, d, J=7.5 Hz), 7.38 (2H, d, J=7.0 Hz), 7.28 (2H, d, J=7.5 Hz), 6.40–5.80 (1H, bs), 5.19 (1H, d, J=8.0 Hz), 4.40–4.05 (5H, m), 2.98 (2H, t, J=7.0 Hz), 2.50–2.05 (1H, m), 1.16 (3H, t, J=7.0 Hz), 0.95 (3H, d, J=5.5 Hz), 0.88 (3H, d, J=5.5 Hz).

REFERENCE EXAMPLE 2 bis(2-bromobenzyl)ether

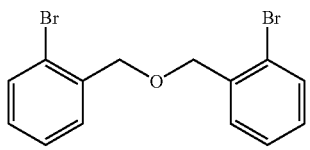

Solution of 2-bromobenzylalcohol (3.8 g) in THF (10 ml) was delivered by drops over 15 minutes to suspension of sodium hydride (0.88 g; 60% in oil) in THF (30 ml) cooled to −0° C. in argon atmosphere, and the reaction mixture was further stirred for 20 minutes. Solution of 2-bromobenzyl bromide (6.0 g) in THF (10 ml) was added thereto and the reaction solution was stirred for one hour at room temperature. The reaction mixture was poured to water and neutralized with 1N hydrochloric acid and extracted with hexane. The organic layer was dried with anhydrous sodium sulfate and concentrated. The residue was purified by column chromatography (hexane:ethyl acetate=1:0 to 100:1 to 10:1) to obtain the title compound (5.77 g) having the following physical data.

TLC: Rf 0.24 (hexane) NMR (CDCl$_3$): δ7.56 (4H, d, J=8 Hz), 7.33 (2H, t, J=8 Hz), 7.15 (2H, t, J=8 Hz), 4.71 (4H, s).

EXAMPLE 2 bis[2-(hydroxyphenylboryl)benzyl]ether

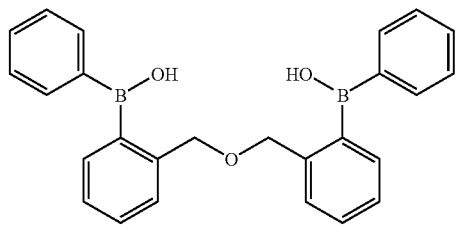

1.6M n-butyllithium (1.4 ml) was delivered by drops at −78° C. to solution of the compound produced in Reference Example 2 (356 mg) in THF (10 ml) and the reaction mixture was stirred for one hour. Diisopropoxyphenylboran (0.55 ml) was added thereto and stirred for two hours at room temperature. 1N hydrochloric acid was added to the reaction solution and the water layer was extracted by ethyl acetate. The organic layer was dried with anhydrous sodium sulfate and concentrated. The residue was purified by column chromatography and the obtained solid was recrystallized by isopropyl ether/hexane to obtain the title compound (173 mg) having the following physical data.

TLC: Rf 0.27 (ethyl acetate:hexane=1:3) NMR (CDCl$_3$): δ7.6–7.8 (6H, m), 7.2–7.4 (8H, m), 5.06 (4H, s).

EXAMPLES 2(1) to 2(2)

The same operations in Reference Example 2 to Example 2 were performed using corresponding compounds to obtain the following compounds having the following physical data.

EXAMPLE 2(1)

1,4-bis(4-(hydroxyphenylboryl)phenoxy)butane

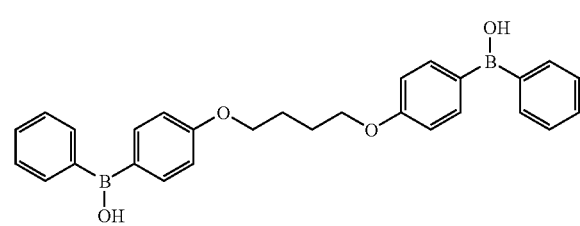

TLC: Rf 0.25 (hexane:ethyl acetate=2:1); NMR (CDCl$_3$): δ7.68 (8H, m), 7.50 (6H, m), 6.96 (4H, d, J=9.0 Hz), 5.75 (2H, s), 4.08 (4H, t, J=4.0 Hz), 2.02 (4H, t, J=4.0 Hz).

EXAMPLE 2(2)

bis[4-(hydroxyphenylboryl)benzyl]ether

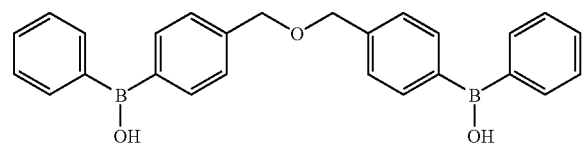

TLC: Rf 0.31 (hexane:ethyl acetate=2:1); NMR (CDCl$_3$): δ8.25 (d, J=6.6 Hz, 2H), 7.88–7.74 (m, 6H), 7.64–7.32 (m, 10H), 5.85 (s, 2H), 4.66 (s, 4H).

EXAMPLE 3 bis(3-chloro-4-methylphenyl)borate

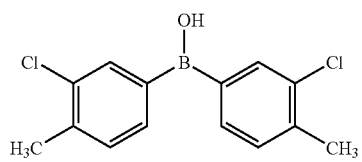

After ignition drying of magnesium piece (0.97 g) in vacuo and purging with argon, anhydrous THF (40 ml) and 1,2-dibromoethane (a few drops) were added. Solution of 3-chloro-4-methylphenyl bromide (6.2 g) in THF (20 ml) was delivered by drops to the mixture over one hour at room temperature and the reaction mixture was heated to reflux for 30 minutes. The reaction mixture was cooled to room temperature and added slowly to solution of trimethyl borate (1.36 ml) in THF (20 ml) cooled to −78° C. and the mixture was left standing to be warmed to room temperature. 1N hydrochloric acid (100 ml) was added to the reaction mixture and the water layer was extracted with ethyl acetate. The organic layer was dried with anhydrous sodium sulfate and concentrated. The residue was purified by column chromatography (ethyl acetate:hexane=1:1), and the obtained solid was recrystalized to obtain the title compound (2.89 g) having the following physical data.

TLC: Rf 0.38 (ethyl acetate:hexane=1:1); NMR (200 MHz, CDCl$_3$): δ7.72 (2H, s), 7.53 (2H, d, J=7 Hz), 7.29 (2H, d, J=7 Hz), 5.7–6.0 (1H, br), 2.45 (6H, s).

EXAMPLE 3(1)

bis[4-(2-(methoxycarbonyl)vinyl)phenyl]borate

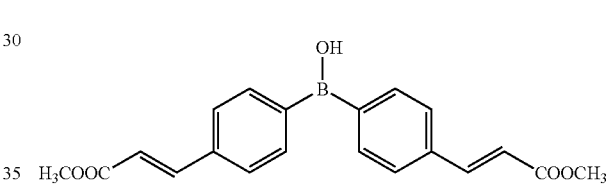

The same operations in Example 3 were performed using corresponding compounds to obtain the following compound having the following physical data.

TLC: Rf 0.28 (hexane:ethyl acetate=3:1); NMR (CD$_3$OD): δ7.70 (2H, d, J=17 Hz), 7.58 (8H, s), 6.56 (2H, d, J=17 Hz), 3.79 (6H, s).

EXAMPLE 4

2-cyclohexylaminoethyl bis(3-chloro-4-methylphenyl)borate

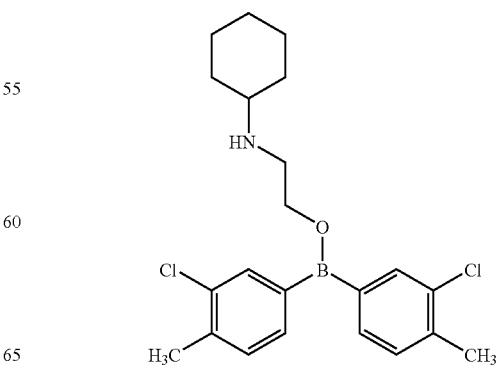

Solution of the compound produced in Example 3 (100 mg) and N-cyclohexylethanolamine (52 mg) in ethanol (10 ml) was stirred overnight at room temperature. The reaction solution was concentrated and the obtained solid was recrystallized by ethanol/isopropyl ether to obtain the title compound (105 mg) having the following physical data.

TLC: Rf 0.27 (acetonitrile:water=3:1, reverse phase); NMR(CDCl$_3$): δ7.44 (2H, s), 7.23 (2H, d, J=8 Hz), 7.11 (2H, d, J=8 Hz), 3.92 (2H, t, J=7 Hz), 2.92 (2H, t, J=7 Hz), 2.50–2.75 (1H, br), 2.32 (6H, s), 1.8–2.0 (2H, br), 1.5–1.7 (4H, br), 0.9–1.2 (4H, br).

EXAMPLES 4(1) to 4(53)

The same operations in Example 4 were performed using the compounds produced in Example 1(1) and Example 2, the compounds produced by performing the same operations in Reference Example 1 to Example 1 using the corresponding compounds, or the compounds produced by performing the same operations in Example 3 using the corresponding compounds, and using the corresponding alcohol compounds to obtain the following compounds.

EXAMPLE 4(1)

2-aminoethyl bis(4-trifluoromethylphenyl)borate

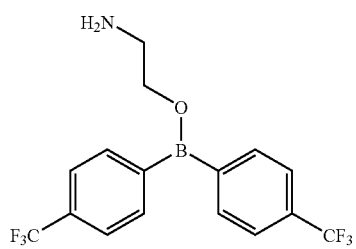

TLC: Rf 0.30 (acetonitrile:water=3:1, reverse phase); NMR (CDCl$_3$): δ7.64 (4H, d, J=8 Hz), 7.52 (4H, d, J=8 Hz), 5.43 (2H, br), 4.00 (2H, t, J=6 Hz), 3.05 (2H, m).

EXAMPLE 4(2)

dicyclopentylborate 2-aminoethyl

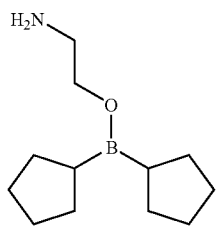

TLC: Rf 0.34 (acetonitrile:water=3:1, reverse phase); NMR (CDCl$_3$+d$_6$-DMSO(5 drops): δ4.35–4.00 (2H, bs), 3.90 (2H, t, J=6.0 Hz), 2.95 (2H, m), 1.80–1.28 (12H, m), 1.28–0.98 (4H, m), 0.95–0.68 (2H, m).

EXAMPLE 4(3)

2-aminoethyl bis(4-chloro-2-methylphenyl)borate

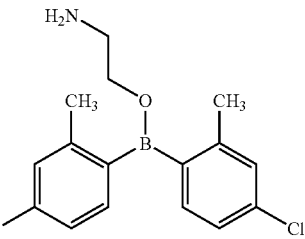

TLC: Rf 0.48 (acetonitrile:water=3:1, reverse phase); NMR (CDCl$_3$+d$_6$-DMSO(2 drops): δ7.38 (2H, d, J=7.5 Hz), 7.08 (2H, dd, J=7.5, 2.0 Hz) 6.98 (2H, d, J=2.0 Hz), 5.40–4.70 (2H, bs), 3.92 (2H, t, J=6.5 Hz), 3.04 (2H, t, J=6.5 Hz), 2.12 (6H, s).

EXAMPLE 4(4)

2-aminoethyl bis(4-dimethylaminosulfonylphenyl)borate

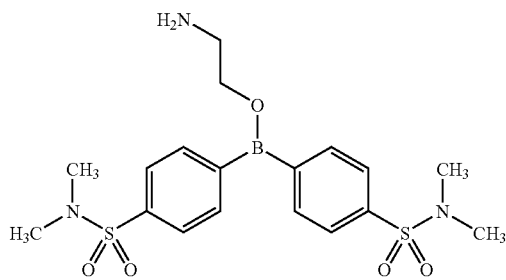

TLC: Rf 0.34 (acetonitrile:water=2:1, reverse phase); NMR (CDCl$_3$+d$_6$-DMSO(10 drops)): δ8.18 (2H, d, J=7.5 Hz), 7.76 (4H, d, J=7.5 Hz), 7.64 (2H, d, J=7.5 Hz), 3.72 (2H, bs), 2.94 (2H, bs), 2.68 (6H, s), 2.64 (6H, s).

EXAMPLE 4(5)

2-aminoethyl bis(2-naphthyl)borate

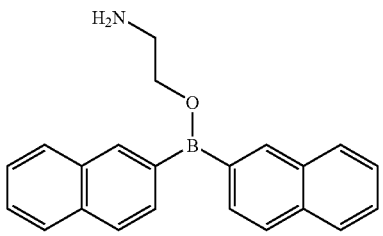

TLC: Rf 0.25 (acetonitrile:water=3:1, reverse phase); NMR (CD$_3$OD): δ8.10–7.84 (2H, m), 7.86–7.50 (8H, m), 7.35 (4H, d, J=4.0 Hz), 4.02 (2H, t, J=6.3, O—CH2), 3.08 (2H, t, J=6.3 Hz, N—CH2).

EXAMPLE 4(6)

2-aminoethyl bis(4-chloro-3-methylphenyl)borate

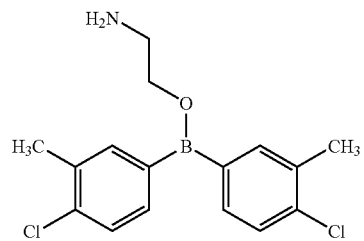

TLC: Rf 0.35 (acetonitrile:water=3:1, reverse phase); NMR (CDCl$_3$+d$_6$-DMSO(2 drops)): δ7.35 (2H, s), 7.19 (4H, s), 5.12 (2H, bs), 3.96 (2H, t, J=6.2 Hz), 3.00 (2H, bm), 2.32 (6H, s).

EXAMPLE 4(7)

2-aminoethyl bis(3-chloro-4-methylphenyl)borate

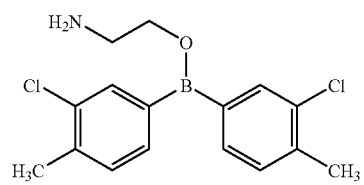

TLC: Rf 0.38 (acetonitrile:water=3:1, reverse phase); NMR (CDCl$_3$+d$_6$-DMSO(4 drops)): δ7.38 (2H, s), 7.17 (2H, d, J=8.2 Hz), 7.10 (2H, d, J=8.2 Hz), 4.87 (2H, s), 3.90 (2H, t, J=6.3 Hz), 2.92 (2H, bs), 2.30 (6H, s).

EXAMPLE 4(8)

2-aminoethyl bis(3,5-dichlorophenyl)borate

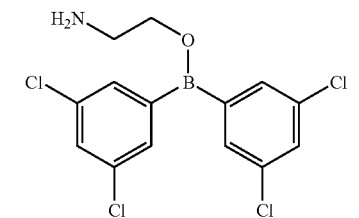

TLC: Rf 0.40 (acetonitrile:water=3:1, reverse phase); NMR (CDCl$_3$+d$_6$-DMSO(5 drops)): δ7.35 (4H, d, J=2.0 Hz), 7.13 (2H, dd, J=2.0, 2.0 Hz), 5.90 (2H, bs), 3.93 (2H, t, J=5.5 Hz), 3.00 (2H, tdd, J=5.5, 5.0, 5.0 Hz).

EXAMPLE 4(9)

2-pyridylmethyl bis(3-chloro-4-methylphenyl)borate

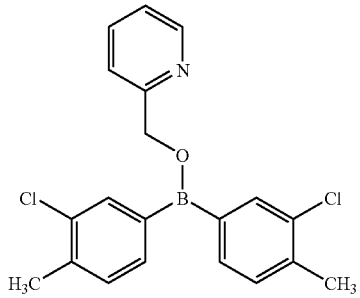

TLC: Rf 0.21 (ethyl acetate:hexane=1:1); NMR (CDCl$_3$): δ8.35 (1H, d, J=5 Hz), 8.02 (1H, t, J=5 Hz), 7.57 (1H, d, J=5 Hz), 7.53 (1H, t, J=5 Hz), 7.29 (2H, s), 7.05–7.20 (4H, m), 5.28 (2H, s), 2.32 (6H, s).

EXAMPLE 4(10)

2-dimethylaminoethyl bis(3-chloro-4-methylphenyl)borate

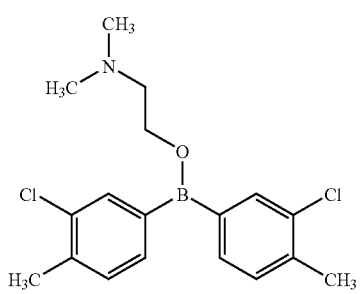

TLC: Rf 0.28 (acetonitrile:water=3:1, reverse phase); NMR (CDCl$_3$): δ7.65 (2H, s), 7.49 (2H, d, J=8 Hz), 7.12 (2H, d, J=8 Hz), 4.26 (2H, t, J=7 Hz), 2.92 (2H, t, J=7 Hz), 2.58 (6H, s), 2.31 (6H, s).

EXAMPLE 4(11)

1-methyl-2-aminoethyl bis(3-chloro-4-methylphenyl)borate

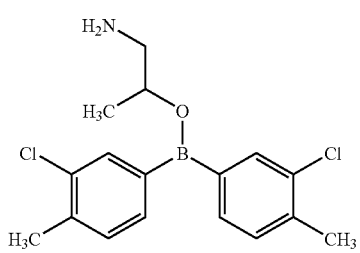

TLC: Rf 0.28 (acetonitrile:water=3:1, reverse phase); NMR (CDCl$_3$): δ7.32 (2H, s), 7.10 (4H, s), 3.9–4.2 (3H, br), 2.9– 3.1 (1H, br), 2.2–2.6 (1H, br), 2.32 (6H, s), 1.27 (3H, d, J=7 Hz).

EXAMPLE 4(12)

2-(phenylamino)ethyl bis(3-chloro-4-methylphenyl)borate

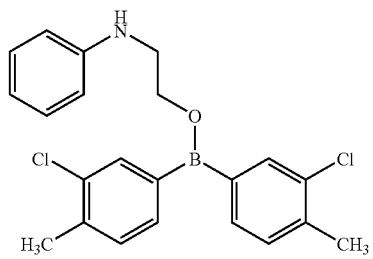

TLC: Rf 0.28 (acetonitrile:water=3:1, reverse phase); NMR (CDCl$_3$): δ7.5–7.7 (2H, br), 7.3–7.5 (2H, br), 7.25 (2H, d, J=8 Hz), 7.17 (2H, d, J=8 Hz), 6.76 (1H, t, J=8 Hz), 6.66 (2H, d, J=8 Hz), 3.9–4.1 (2H, br), 3.38 (2H, t, J=7 Hz), 2.42 (s, 6H).

EXAMPLE 4(13)

2-amino-4-guanidino-1-oxobutyl bis(4-chlorophenyl)borate

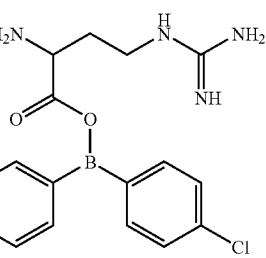

TLC: Rf 0.65 (acetonitrile:water=3:1, reverse phase).

EXAMPLE 4(14)

2-(benzylamino)ethyl bis(3-chloro-4-methylphenyl)borate

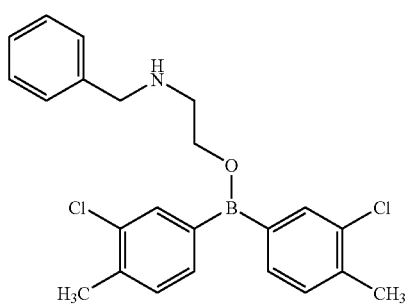

TLC: Rf 0.27 (acetonitrile:water=3:1, reverse phase); NMR (CDCl$_3$): δ7.10–7.50 (11H, m), 3.90–4.10 (2H, br), 3.64 (2H, s), 2.85 (2H, t, J=7 Hz), 2.35 (6H, s).

EXAMPLE 4(15)

(3-benzyl-1,2,3-triazol-4-yl)methyl bis(3-chloro-4-methylphenyl)borate

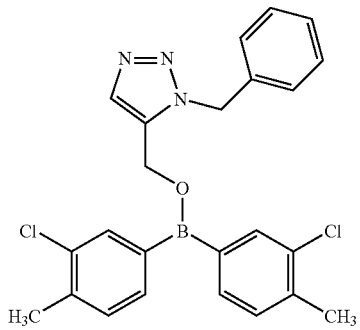

TLC: Rf 0.33 (acetonitrile:water=2:1, reverse phase); NMR (d$_6$-DMSO): δ7.83 (1H, s), 7.62 (2H, s), 7.47 (2H, d, J=7.5 Hz), 7.32 (7H, m), 5.55 (2H, s), 4.55 (1H, s), 4.52 (1H, s), 2.39 (6H, s).

EXAMPLE 4(16)

2-phenyl-2-aminoethyl bis(3-chloro-4-methylphenyl)borate

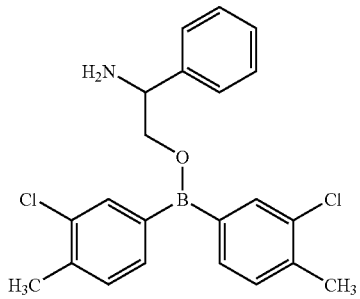

TLC: Rf 0.25 (acetonitrile:water=3:1, reverse phase); NMR (CDCl$_3$): δ7.40 (2H, s), 7.25–7.40 (3H, m), 7.00–7.25 (6H, m), 4.30–4.70 (2H, br), 4.10–4.30 (2H, br), 3.90 (1H, t, J=10 Hz), 2.32 (6H, s).

EXAMPLE 4(17)

2-(piperazin-1-yl)ethyl bis(3-chloro-4-methylphenyl)borate

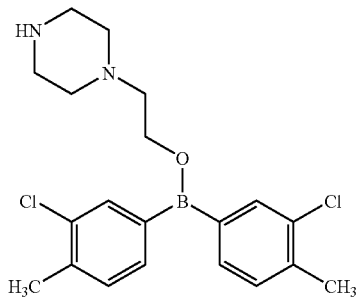

TLC: Rf 0.27 (acetonitrile:water=3:1, reverse phase); NMR (CDCl$_3$): δ7.26 (2H, s), 7.10 (2H, d, J=8 Hz), 6.90 (2H, d, J=8 Hz), 3.55 (2H, t, J=7 Hz), 2.97 (4H, t, J=6 Hz)), 2.58 (4H, t, J=6 Hz), 2.48 (2H, t, J=7 Hz), 2.14 (6H, s).

EXAMPLE 4(18)

2-(butylamino)ethyl bis(3-chloro-4-methylphenyl)borate

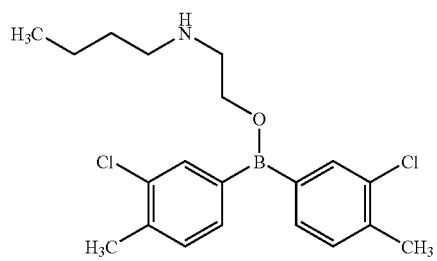

TLC: Rf 0.28 (acetonitrile:water=3:1, reverse phase); NMR (CDCl$_3$): δ7.43 (2H, s), 7.22 (2H, d, J=8 Hz), 7.13 (2H, d, J=8 Hz), 4.00 (2H, t, J=7 Hz), 2.90–3.05 (2H, br), 2.54 (2H, t, J=7 Hz), 2.33 (6H, s), 1.35–1.55 (2H, m), 1.15–1.35 (2H, m), 0.87 (3H, t, J=7 Hz).

EXAMPLE 4(19)

1-phenyl-1-(2-pyridyl)methyl bis(3-chloro-4-methylphenyl)borate

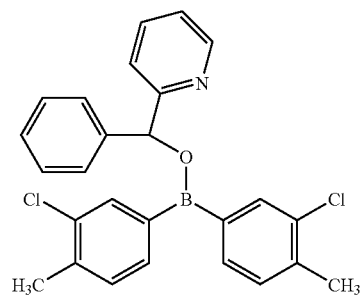

TLC: Rf 0.58 (ethyl acetate:hexane=1:1); NMR (CDCl$_3$): δ8.38 (1H, d, J=5 Hz), 7.93 (1H, t, J=8 Hz), 7.1–7.6 (13H, m), 6.07 (1H, s), 2.36 (3H, s), 2.34 (3H, s).

EXAMPLE 4(20)

2-amino-2-(methoxycarbonyl)ethyl bis(4-chlorophenyl)borate

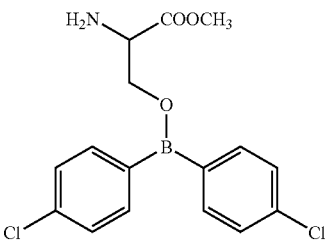

TLC: Rf 0.45 (acetonitrile:water=3:1, reverse phase); NMR (CDCl$_3$): δ7.26 (8H, m), 5.05–4.50 (2H, bs), 4.13 (1H, dd, J=10, 5.5 Hz), 3.90 (2H, m), 3.80 (3H, s).

EXAMPLE 4(21)

1-benzyl-2-(methylamino)ethyl bis(3-chloro-4-methylphenyl)borate

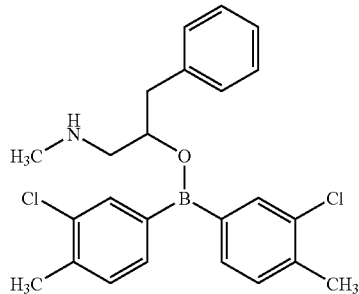

TLC: Rf 0.26 (acetonitrile:water=3:1, reverse phase); NMR (CDCl$_3$): δ7.42 (2H, s), 7.05–7.35 (9H, m), 4.2–4.4 (1H, br), 3.8–4.1 (1H, br), 3.22 (1H, dd, J=14, 5 Hz), 2.91 (1H, dd, J=14, 5 Hz), 2.9–3.1 (1H, br), 2.4–2.7 (1H, br), 2.35 (3H, s), 2.33 (3H, s), 2.28 (3H, s).

EXAMPLE 4(22)

1-phenyl-2-aminoethyl bis(3-chloro-4-methylphenyl)borate

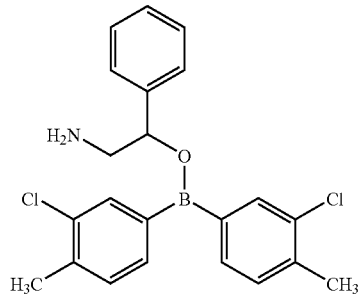

TLC: Rf 0.26 (acetonitrile:water=3:1, reverse phase); NMR (CDCl₃): δ7.05–7.45 (11H, m), 4.87 (1H, dd, J=10, 5 Hz), 4.0–4.3 (2H, br), 3.1–3.3 (1H, br), 2.5–2.7 (1H, br), 2.36 (3H, s), 2.33 (3H, s).

EXAMPLE 4(23)

1-(4-chlorophenoxymethyl)-2-(methylamino)ethyl bis(3-chloro-4-methylphenyl)borate

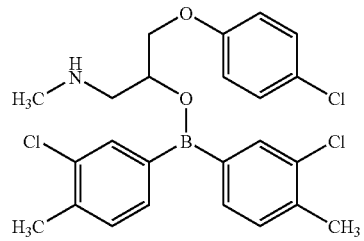

TLC: Rf 0.56 (acetonitrile:water=3:1, reverse phase); NMR (CDCl₃): δ7.50 (2H, s), 7.31–7.13 (6H, m), 7.06 (1H, d, J=8.0 Hz), 6.79 (2H, bd, J=7.5 Hz), 4.80–4.35 (2H, bs), 4.11 (2H, s), 3.30–2.70 (2H, bs), 2.22 (3H, d, J=4.6 Hz), 2.33 (3H, s), 2.29 (3H, s).

EXAMPLE 4(24)

1-phenyl-2-(1-(ethoxycarbonyl)piperidin-4-ylamino) ethyl

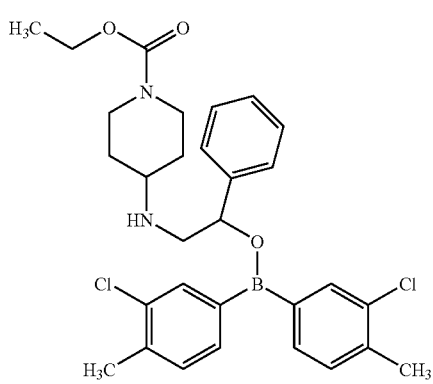

TLC: Rf 0.43 (acetonitrile:water=3:1, reverse phase); NMR (CDCl₃): δ7.56 (4H, bs), 7.50–7.24 (5H, m), 7.08 (2H, bs), 4.94 (1H, dd, J=12, 4.5 Hz), 4.22–3.90 (2H, m), 4.08 (2H, q, J=6.8 Hz), 3.38 (1H, m), 2.82 (1H, m), 2.72–2.20 (3H, m), 2.38 (6H, s), 2.10–1.75 (2H, m), 1.48–1.18 (2H, m), 1.22 (3H, t, J=6.8 Hz).

EXAMPLE 4(25)

1-(methylaminomethyl)nonyl bis(3-chloro-4-methylphenyl)borate

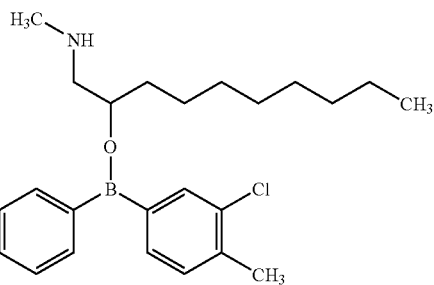

TLC: Rf 0.28 (acetonitrile:water=2:1, reverse phase); NMR (CDCl₃): δ7.48 (2H, d, J=3.5 Hz), 7.26 (2H, m), 7.19 (1H, d, J=7.5 Hz), 7.08 (1H, d, J=7.5 Hz), 4.08 (1H, bs), 3.09 (1H, bs), 3.18 (1H, bs), 2.35 (6H, s), 2.32 (3H, s), 1.80 (1H, m), 1.70–1.20 (m, 14H), 0.88 (3H, t, J=7.0 Hz).

EXAMPLE 4(26)

3-phenyl-1-(2-pyridyl)propyl bis(3-chloro-4-methylphenyl)borate

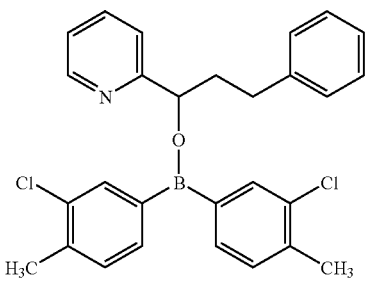

TLC: Rf 0.61 (ethyl acetate:hexane=1:1); NMR (CDCl₃): δ8.32 (1H, d, J=5 Hz), 7.95 (1H, t, J=8 Hz), 7.35–7.50 (3H, m), 7.05–7.30 (10H, m), 5.26 (1H, dd, J=8, 3 Hz), 2.9–3.1 (2H, m), 2.30 (6H, d, J=5 Hz), 2.1–2.4 (2H, m).

EXAMPLE 4(27)

cis-3-phenyl-1-(2-pyridyl)-2-propenyl bis(3-chloro-4-methylphenyl)borate

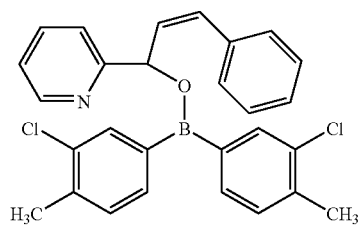

TLC: Rf 0.59 (ethyl acetate:hexane=1:1); NMR (CDCl₃): δ8.32 (1H, d, J=5 Hz), 8.00 (1H, t, J=8 Hz), 7.05–7.60 (13H, m), 6.94 (1H, d, J=10 Hz), 6.02 (1H, d, J=10 Hz), 5.92 (1H, t, J=10 Hz), 2.31 (6H, d, J=1 Hz).

EXAMPLE 4(28)

1-(5-methylimidazol-4-yl)-1-phenylmethyl bis(3-chloro-4-methylphenyl)borate

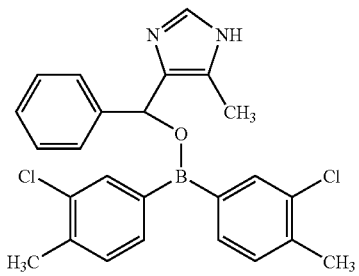

TLC: Rf 0.28 (acetonitrile:water=3:1, reverse phase); NMR (DMSO-$d_6$): δ8.67 (1H, s), 7.1–7.5 (11H, m), 5.80 (1H, s), 2.22 (6H, s), 1.80 (3H, s).

EXAMPLE 4(29)

1-(2-imidazolyl)-1-phenylmethyl bis(3-chloro-4-methylphenyl)borate

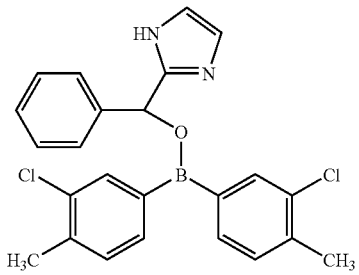

TLC: Rf 0.28 (acetonitrile:water=3:1, reverse phase); NMR (DMSO-$d_6$): δ7.57 (1H, s), 7.10–7.45 (12H, m), 6.08 (1H, s), 2.23 (6H, s).

EXAMPLE 4(30)

1-(2-pyridyl)ethyl bis(3-chloro-4-methylphenyl)borate

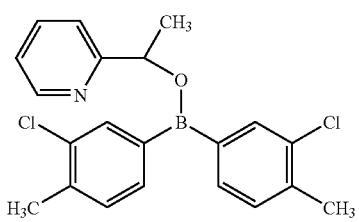

TLC: Rf 0.44 (ethyl acetate:hexane=1:1); NMR (CDCl$_3$): δ8.30 (1H, d, J=5 Hz), 8.04 (1H, t, J=6 Hz), 7.45–7.55 (2H, m), 7.32 (1H, s), 7.05–7.25 (m, 5H), 5.32 (1H, q, J=7 Hz), 2.32 (6H, s), 1.71 (3H, d, J=7 Hz).

EXAMPLE 4(31)

1-(2-pyridyl)-2-propenyl bis(3-chloro-4-methylphenyl)borate

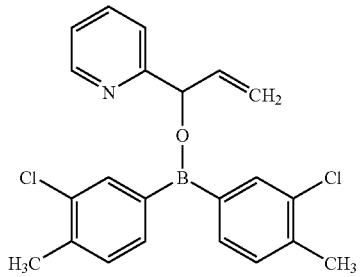

TLC: Rf 0.53 (ethyl acetate:hexane=1:1); NMR (CDCl$_3$): δ8.32 (1H, d, J=6 Hz), 8.06 (1H, t, J=8 Hz), 7.53 (2H, t, J=8 Hz), 7.35 (1H, s), 7.05–7.25 (m, 5H), 6.10 (1H, ddd, J=18, 10, 8 Hz), 5.62 (1H, d, J=18 Hz), 5.60 (1H, d, J=8 Hz), 5.43 (1H, d, J=10 Hz), 2.25 (6H, s).

EXAMPLE 4(32)

1-methyl-1-(2-pyridyl)ethyl bis(3-chloro-4-methylphenyl)borate

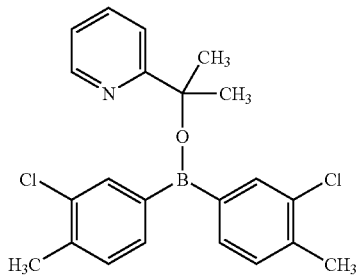

TLC: Rf 0.50 (ethyl acetate:hexane=1:1); NMR (CDCl$_3$): δ8.31 (1H, d, J=5 Hz), 8.06 (1H, t, J=6 Hz), 7.50–7.60 (2H, m), 7.24 (2H, s), 7.11 (2H, d, J=6 Hz), 7.08 (2H, d, J=6 Hz), 2.50 (6H, s), 1.60 (6H, s).

EXAMPLE 4(33)

1-phenyl-1-(2-aminophenyl)methyl bis(3-chloro-4-methylphenyl)borate

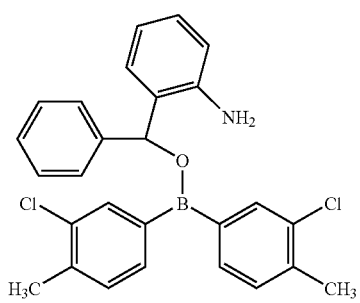

TLC: Rf 0.27 (acetonitrile:water=3:1, reverse phase); NMR (CD$_3$OD): δ6.95–7.55 (15H, m), 6.70 (1H, d, J=8 Hz), 5.68 (1H, s), 2.27 (6H, s).

EXAMPLE 4(34)

(1S,2R)-1,2-diphenyl-2-aminoethyl bis(3-chloro-4-methylphenyl)borate

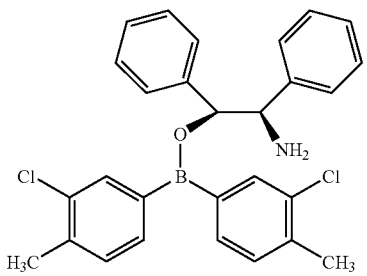

TLC: Rf 0.25 (acetonitrile:water=3:1, reverse phase); NMR (CDCl$_3$): δ7.62 (1H, s), 7.50 (1H, s), 7.47 (1H, d, J=9 Hz), 7.30 (1H, d, J=8 Hz), 6.9–7.2 (10H, m), 6.8–6.9 (2H, m), 5.33 (1H, d, J=5 Hz), 4.45–4.70 (3H, br), 2.35 (6H, s).

EXAMPLE 4(35)

(1R,2S)-1,2-diphenyl-2-aminoethyl bis(3-chloro-4-methylphenyl)borate

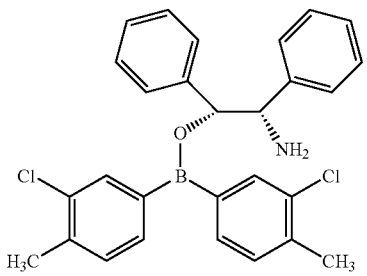

TLC: Rf 0.25 (acetonitrile:water=3:1, reverse phase); NMR (CDCl$_3$): δ7.62 (1H, s), 7.50 (1H, s), 7.47 (1H, d, J=9 Hz), 7.30 (1H, d, J=8 Hz), 6.9–7.2 (10H, m), 6.8–6.9 (2H, m), 5.33 (1H, d, J=5 Hz), 4.45–4.70 (3H, br), 2.35 (6H, s).

EXAMPLE 4(36)

1-phenyl-1-(pyradin-2-yl)methyl bis(3-chloro-4-methylphenyl)borate

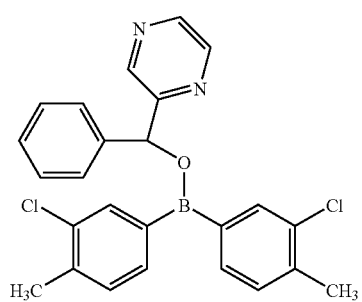

TLC: Rf 0.26 (acetonitrile:water=3:1, reverse phase); NMR (CDCl$_3$): δ8.92 (1H, d, J=3 Hz), 8.73 (1H, s), 8.36 (1H, d, J=3 Hz), 7.4–7.6 (6H, m), 7.1–7.3 (5H, m), 6.20 (1H, s), 2.35 (6H, s).

EXAMPLE 4(37)

1-(dimethylaminomethyl)-2-dimethylaminoethyl bis(3-chloro-4-methylphenyl)borate

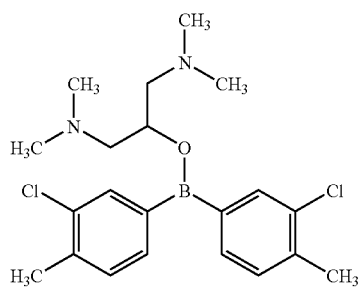

TLC: Rf 0.27 (acetonitrile:water=3:1, reverse phase); NMR (CDCl$_3$): δ7.68 (2H, s), 7.47 (2H, d, J=8 Hz), 7.10 (2H, d, J=8 Hz), 4.3–4.5 (1H, br), 2.6–2.9 (4H, br), 2.46 (12H, s), 2.30 (6H, s).

EXAMPLE 4(38)

1-(pyrazol-3-yl)-1-phenylmethyl bis(3-chloro-4-methylphenyl)borate

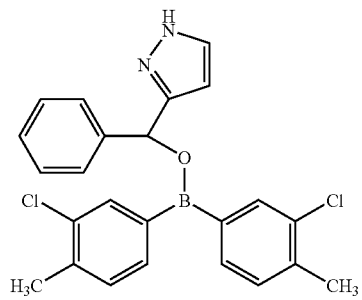

TLC: Rf 0.25 (acetonitrile:water=3:1, reverse phase); NMR (CD$_3$OD): δ6.7–7.6 (13H, m), 6.22 (1H, d, J=3 Hz), 2.35 (6H, s).

EXAMPLE 4(39)

1-(4-trifluoromethylphenyl)-1-(2-pyridyl)methyl bis(3-chloro-4-methylphenyl)borate

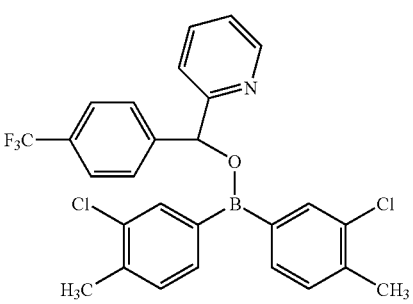

TLC: Rf 0.57 (ethyl acetate:hexane=1:1); NMR (CDCl₃): δ8.41 (1H, d, J=5 Hz), 7.97 (1H, t, J=8 Hz), 7.60–7.75 (4H, m), 7.57 (1H, t, J=5 Hz), 7.43 (1H, s), 7.20–7.30 (3H, m), 7.10–7.20 (3H, m), 6.12 (1H, s), 2.35 (3H, s), 2.34 (3H, s).

EXAMPLE 4(40)

1-(4-acetylamino)phenyl-1-(2-pyridyl)methyl bis(3-chloro-4-methylphenyl)borate

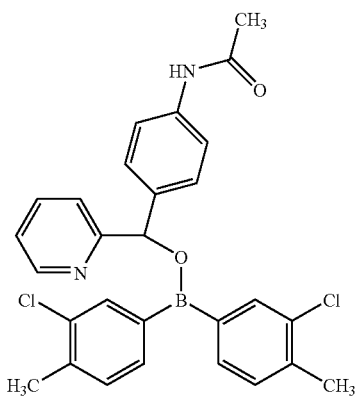

TLC: Rf 0.13 (ethyl acetate:hexane=3:1); NMR (CDCl₃): δ8.36 (1H, d, J=5 Hz), 7.94 (1H, t, J=8 Hz), 7.63 (1H, s), 7.35–7.55 (6H, m), 7.24 (2H, d, J=4 Hz), 7.23 (1H, t, J=8 Hz), 7.10–7.20 (3H, m), 6.04 (1H, s), 2.32 (6H, s), 2.11 (3H, s).

EXAMPLE 4(41)

2-aminoethyl bis(4-chloro-3-trifluoromethylphenyl)borate

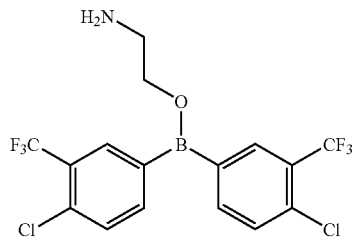

TLC: Rf 0.26 (acetonitrile:water=3:1, reverse phase); NMR (DMSO-d₆): δ7.82 (2H, s), 7.64 (2H, d, J=8 Hz), 7.50 (2H, d, J=8 Hz), 6.30–6.55 (2H, br), 3.78 (2H, t, J=7 Hz), 2.89 (2H, t, J=7 Hz).

EXAMPLE 4(42)

1-(3-chloropyridin-2-yl)-1-phenylmethyl bis(3-chloro-4-methylphenyl)borate

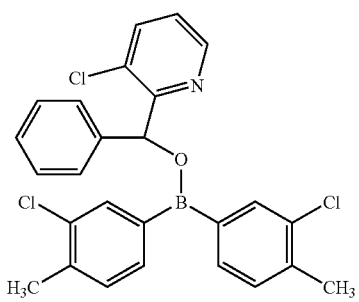

TLC: Rf 0.56 (ethyl acetate:hexane=1:1); NMR (CDCl₃): δ8.39 (1H, d, J=5 Hz), 7.93 (1H, d, J=8 Hz), 7.57 (1H, dd, J=8, 5 Hz), 7.10–7.45 (11H, m), 6.24 (1H, s), 2.35 (6H, s).

EXAMPLE 4(43)

2-aminoethyl bis(3,5-di(trifluoromethyl)phenyl)borate

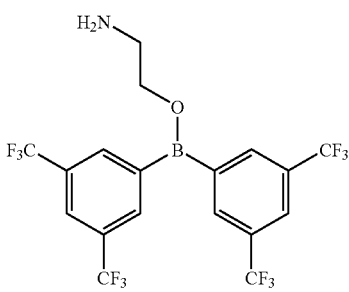

NMR (DMSO-d₆): δ8.03 (4H, s), 7.75 (2H, s), 6.5–6.7 (2H, br), 3.83 (2H, t, J=6 Hz), 2.81 (2H, t, J=6 Hz).

EXAMPLE 4(44)

2-aminoethyl bis(3,4,5-trifluorophenyl)borate

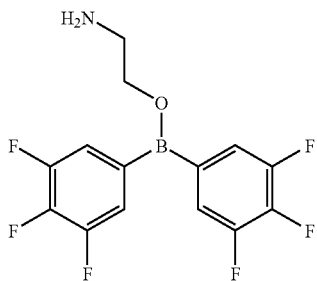

NMR (DMSO-d₆): δ7.0–7.2 (4H, m), 6.2–6.4 (2H, br), 3.74 (2H, t, J=6 Hz), 2.86 (2H, t, J=6 Hz).

EXAMPLE 4(45)

2-aminoethyl bis(2,3,4-trifluorophenyl)borate

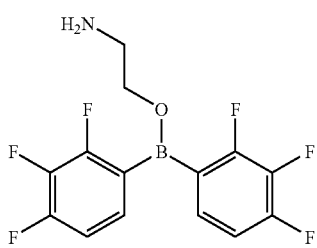

NMR (DMSO-d$_6$): δ7.08 (2H, d, J=4 Hz), 7.03 (2H, d, J=4 Hz), 6.45–6.65 (2H, br), 3.73 (2H, t, J=6 Hz), 2.91 (2H, t, J=6 Hz).

EXAMPLE 4(46)

2-aminoethyl bis(3-chloro-4-(1,1-dimethylethyl)phenyl)borate

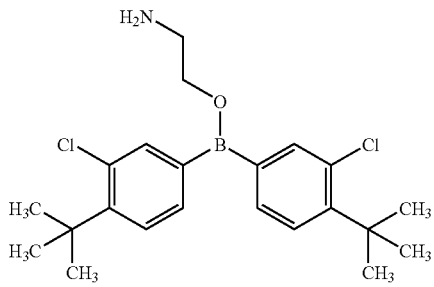

TLC: Rf 0.08 (acetonitrile:water=3:1, reverse phase); NMR (CDCl$_3$-CD$_3$OD): δ7.37 (2H, s), 7.30 (2H, d, J=8 Hz), 7.15 (2H, d, J=8 Hz), 3.82 (2H, t, J=7 Hz), 2.85 (2H, t, J=7 Hz), 1.44 (18H, s).

EXAMPLE 4(47)

1-(4-nitropyridin-2-yl)-1-phenylmethyl bis(3-chloro-4-(methylphenyl)borate

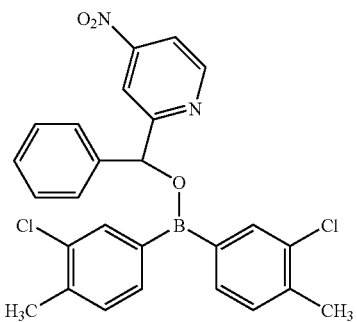

TLC: Rf 0.68 (ethyl acetate:hexane=1:1); NMR (CDCl$_3$): δ8.64 (1H, d, J=6 Hz), 8.25 (1H, dd, J=6, 2 Hz), 7.93 (1H, s), 7.4–7.6 (6H, m), 7.26 (2H, s), 7.1–7.2 (3H, m), 6.17 (1H, s), 2.33 (6H, s).

EXAMPLE 4(48)

1-(4-bromopyridin-2-yl)-1-phenylmethyl bis(3-chloro-4-(methylphenyl)borate

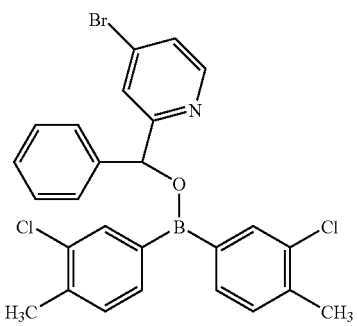

TLC: Rf 0.68 (ethyl acetate:hexane=1:1); NMR (CDCl$_3$): δ8.18 (1H, d, J=5 Hz), 7.66 (1H, d, J=5 Hz), 7.35–7.55 (7H, m), 7.1–7.3 (5H, m), 6.03 (1H, s), 2.33 (6H, s).

EXAMPLE 4(49)

5,6,7,8-tetrahydroquinolin-8-yl bis(3-chloro-4-(methylphenyl)borate

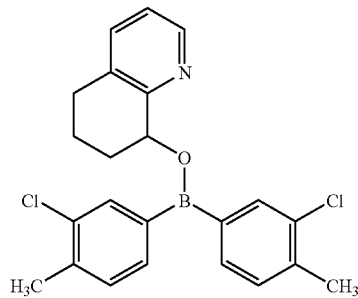

TLC: Rf 0.41 (ethyl acetate:hexane=1:1); NMR (CDCl$_3$): δ8.11 (1H, d, J=6 Hz), 7.72 (1H, d, J=8 Hz), 7.39 (1H, dd, J=8, 6 Hz), 7.0–7.3 (6H, m), 4.84 (1H, dd, J=10, 6 Hz), 2.70–3.05 (2H, m), 2.50–2.70 (1H, m), 2.33 (3H, s), 2.28 (3H, s), 2.10–2.25 (1H, m), 1.7–2.0 (2H, m).

EXAMPLE 4(50)

2-aminoethyl (4-chlorophenyl)(4-chloro-2-methoxyphenyl)borate

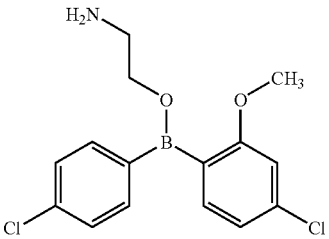

TLC: Rf 0.32 (acetonitrile:water=3:1, reverse phase); NMR (CDCl$_3$+d$_6$-DMSO(5 drops)): δ7.42 (2H, d, J=7.5 Hz), 7.33 (1H, d, J=1.2 Hz), 7.14 (2H, d, J=7.5 Hz), 7.06 (1H, dd, J=8.0, 1.2 Hz), 6.75 (1H, d, J=8.0 Hz), 5.90 (1H, bs), 5.72 (1H, bs), 3.95 (1H, s), 3.82 (3H, s), 3.18–2.80 (3H, m).

EXAMPLE 4(51)

2-aminoethyl (4-chlorophenyl)(1-naphtyl)borate

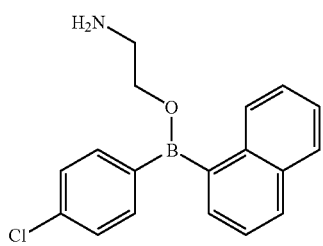

TLC: Rf 0.25 (acetonitrile:water=3:1, reverse phase); NMR (CDCl$_3$+d$_6$-DMSO(10 drops)): δ8.19 (1H, d, J=8.0 Hz), 7.74 (1H, d, J=7.0 Hz), 7.70–7.55 (2H, m), 7.38 (2H, d, J=7.5 Hz), 7.45–7.16 (3H, m), 7.05 (2H, t, J=7.5 Hz), 6.52–6.00 (2H, bs), 4.12–3.64 (2H, t, J=5.5 Hz), 2.98 (2H, m).

EXAMPLE 4(52)

2-aminoethyl (4-chlorophenyl)(1,1'-biphenyl-4-yl)borate

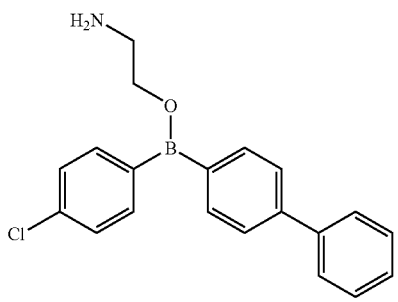

TLC: Rf 0.25 (acetonitrile:water=3:1, reverse phase); NMR (CDCl$_3$+d$_6$-DMSO(3 drops)): δ7.62–7.25 (11H, m), 7.22 (2H, d, J=7.5 Hz), 5.06 (2H, bs), 3.98 (2H, t, J=5.5 Hz), 3.02 (2H, bs).

EXAMPLE 4(53)

2-aminoethyl (4-chlorophenyl)(3-chloro-4-phenoxymethylphenyl)borate

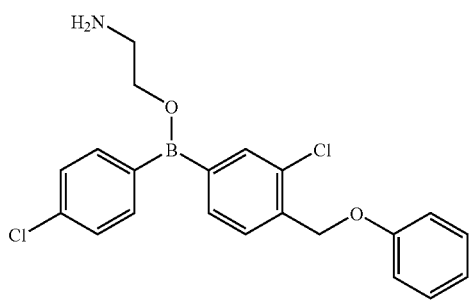

TLC: Rf 0.34 (acetonitrile:water=2:1, reverse phase); NMR (CDCl$_3$): δ7.90–6.88 (12H, m), 5.14 (2H, s), 3.90 (2H, t, J=6.3 Hz), 2.98 (2H, bs).

EXAMPLE 4(54)

2-aminoethyl (4-chlorophenyl)(benzothiazol-2-yl)borate

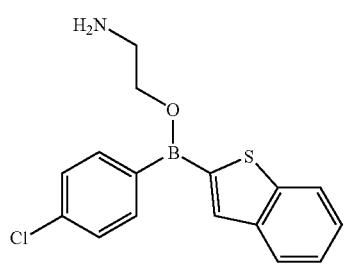

TLC: Rf 0.35 (acetonitrile:water=3:1, reverse phase); NMR (CDCl$_3$+d$_6$-DMSO(10 drops)): δ7.75 (1H, d, J=7.0 Hz), 7.72–7.48 (3H, m), 7.42 (1H, d, J=8.5 Hz), 7.30–7.06 (4H, m), 5.98 (2H, bs), 4.20–3.88 (2H, m).

EXAMPLE 4(55)

2-aminoethyl (4-chlorophenyl)(4-methylnaphthyl-1-yl)borate

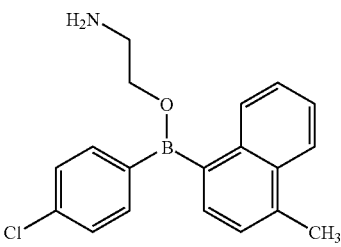

TLC: Rf 0.34 (acetonitrile:water=3:1, reverse phase); NMR (CDCl$_3$+d$_6$-DMSO(10 drops)): δ8.21 (1H, d, J=8.0 Hz), 7.88 (1H, d, J=8.0 Hz), 7.58 (1H, d, J=6.0 Hz), 7.35 (2H, d, J=7.5 Hz), 7.32–7.12 (3H, m), 7.05 (2H, d, J=7.5 Hz), 6.32 (2H, bs), 4.08–3.65 (2H, bm), 2.94 (2H, bs), 2.60 (3H, s).

EXAMPLE 4(56)

2-aminoethyl (3-phenylpropyl)phenylborate

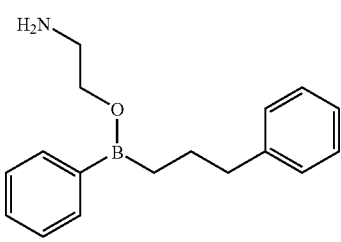

TLC: Rf 0.58 (acetonitrile:water=2:1, reverse phase); NMR (CDCl$_3$+d$_6$-DMSO(2 drops)): δ7.40–7.05 (9H, m), 3.62 (2H, m), 2.78–2.50 (4H, m), 1.98–1.78 (2H, m), 0.82 (2H, t, J=8.0 Hz).

EXAMPLE 4(57)

2-aminoethyl (3,3'-diphenylpropyl)phenylborate

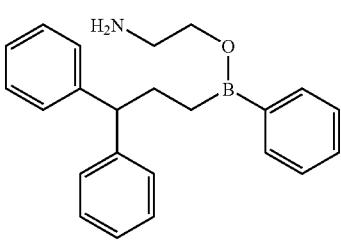

TLC: Rf 0.64 (acetonitrile:water=2:1, reverse phase); NMR (CDCl$_3$+d$_6$-DMSO (1 drops)): δ7.38–7.02 (15H, m), 4.16 (2H, bs), 3.92 (2H, t, J=6.5 Hz), 3.58 (1H, m), 2.82 (2H, bs), 1.85 (2H, m), 0.50 (2H, m).

EXAMPLE 4(58)

2-aminoethyl (2-phenoxyphenyl)phenylborate

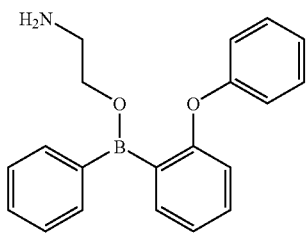

TLC: Rf 0.54 (acetonitrile:water=3:1, reverse phase); NMR (CDCl$_3$, CDCl$_3$+d$_6$-DMSO(2 drops)): δ7.79–7.42 (3H, m), 7.39–7.24 (2H, m), 7.23–6.96 (8H, m), 6.68 (1H, d, J=8.5 Hz), 5.32 (2H, bs), 3.94 (2H, t, J=6.5 Hz), 2.99 (2H, tt, J=6.5, 6.5 Hz).

EXAMPLE 4(59)

2-aminoethyl (4-vinylphenyl)(3,4-dichlorophenyl)borate

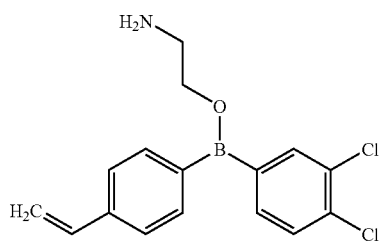

TLC: Rf 0.34 (acetonitrile:water=3:1, reverse phase); NMR (CDCl$_3$+d$_6$-DMSO (10%)): δ7.88 (2H, s), 7.74–6.95 (7H, m), 6.60 (1H, m), 5.62 (1H, dd, J=17, 16 Hz), 5.04 (1H, dd, J=17, 11 Hz), 3.90 (2H, t, J=6.5 Hz), 2.88 (2H, t, J=6.5 Hz).

EXAMPLE 4(60)

2-aminoethyl (4-bromophenyl)(4-chlorophenyl)borate

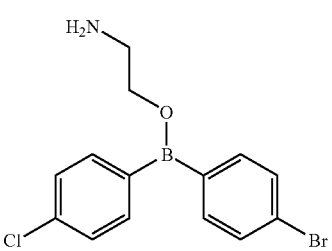

TLC: Rf 0.55 (acetonitrile:water=3:1, reverse phase); NMR (CDCl$_3$ (10%) +d$_6$-DMSO): δ7.38 (2H, d, J=8.5 Hz), 7.31 (4H, m), 7.14 (2H, d, J=8.5 Hz), 6.12 (2H, bs), 3.80 (2H, t, J=6.5 Hz), 2.82 (2H, tt, J=6.5, 6.0 Hz).

EXAMPLE 4(61)

2-aminoethyl (4-chlorophenyl)(4-(1,1-dimethylethyl)phenyl)borate

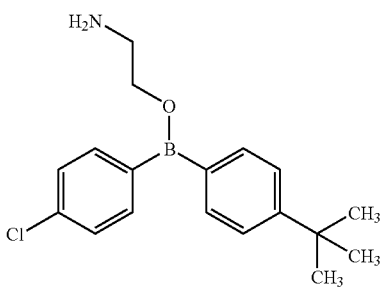

TLC: Rf 0.35 (acetonitrile:water=3:1, reverse phase); NMR (CDCl$_3$): δ7.38 (2H, d, J=7.5 Hz), 7.27 (2H, d, J=7.5 Hz), 7.12 (2H, d, J=7.5 Hz), 7.05 (2H, d, J=7.5 Hz), 6.04–5.60 (2H bs), 3.79 (2H, t, J=6.0 Hz), 2.83 (2H, t, J=6.0 Hz), 1.18 (9H, s).

EXAMPLE 4(62)

2-aminoethyl (4-chlorophenyl)(4-iodophenyl)borate

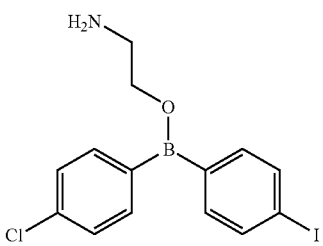

TLC: Rf 0.58 (acetonitrile:water=2:1, reverse phase); NMR (d$_6$-DMSO): δ7.49 (2H, d, J=7.5 Hz), 7.35 (2H, d, J=8.0 Hz), 7.18 (2H, d, J=7.5 Hz), 7.14 (2H, d, J=8.0 Hz), 6.14 (2H, bs), 3.73 (2H, t, J=6.5 Hz), 2.82 (2H, tt, J=6.5, 6.0 Hz).

EXAMPLE 4(63)

2-aminoethyl (4-chlorophenyl)(1,1'-biphenyl-2-yl)borate

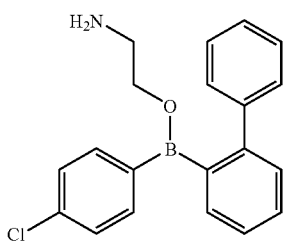

TLC: Rf 0.36 (acetonitrile:water=3:1, reverse phase); NMR (DMSO-$d_6$): δ7.69 (1H, d, J=7 Hz), 7.1–7.3 (5H, m), 6.9–7.1 (7H, m), 5.6–5.8 (2H, br), 3.49 (2H, t, J=6 Hz), 2.69 (2H, t, J=6 Hz).

EXAMPLE 4(64)

2-aminoethyl (3-pyridyl)phenylborate

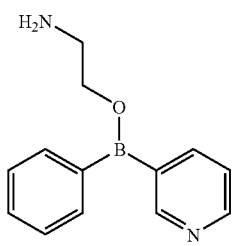

TLC: Rf 0.09 (ethyl acetate:methanol=1:1, borinic acid); NMR (DMSO-$d_6$): δ8.50 (1H, s), 8.23 (1H, d, J=4 Hz), 7.68 (1H, d, J=7 Hz), 7.36 (2H, d, J=8 Hz), 7.0–7.2 (4H, m), 6.05–6.25 (2H, br), 3.75 (2H, t, J=7 Hz), 2.85 (2H, t, J=7 Hz).

EXAMPLE 4(65)

2-aminoethyl (3-pyridyl)(4-chlorophenyl)borate

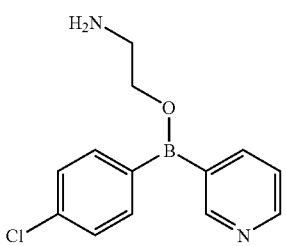

TLC: Rf 0.09 (ethyl acetate: methanol=1:1, borinic acid); NMR (DMSO-$d_6$): δ8.43 (1H, s), 8.18 (1H, d, J=5 Hz), 7.57 (1H, d, J=8 Hz), 7.30 (2H, d, J=8 Hz), 7.12 (2H, d, J=8 Hz), 7.06 (1H, dd, J=8, 5 Hz), 6.0–6.3 (2H, br), 3.68 (2H, t, J=7 Hz), 2.76 (2H, t, J=7 Hz).

EXAMPLE 4(66)

bis[2-[(2-aminoethoxy)phenylboryl]benzyl]ether

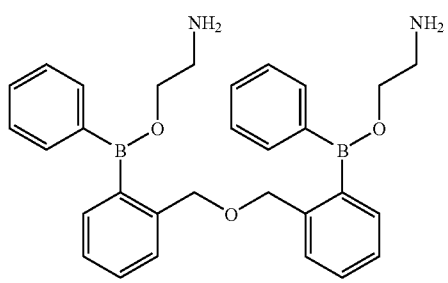

TLC: Rf 0.33 (acetonitrile:water=3:1, reverse phase); NMR (CDCl$_3$): δ7.41 (2H, d, J=5 Hz), 7.10–7.25 (16H, m), 4.7–4.9 (4H, br), 4.42 (4H, s), 3.68 (4H, t, J=6 Hz), 2.4–2.6 (4H, br).

EXAMPLE 4(67)

bis[4-((2-aminoethoxy)phenylboryl)benzyl]ether

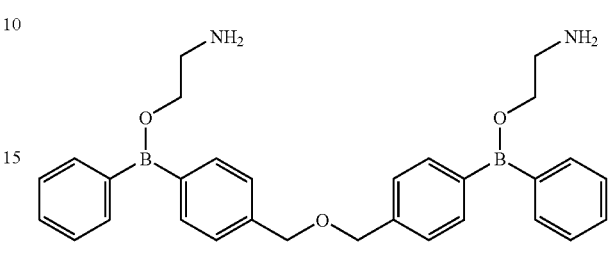

TLC: Rf 0.34 (hexane:ethyl acetate=1:1); NMR (CDCl$_3$): δ7.40–7.29 (m, 8H), 7.16–6.96 (m, 10H), 6.03 (bt, J=7.0 Hz, 4H), 4.36 (s, 4H), 3.74 (t, J=7.0 Hz, 4H), 2.80 (qnt, J=7.0 Hz, 4H).

EXAMPLE 4(68)

[4-[(2-aminoethoxy)phenylboryl]benzyl][2-[4[(2-aminoethoxy)phenylboryl]phenyl]ethyl]ether

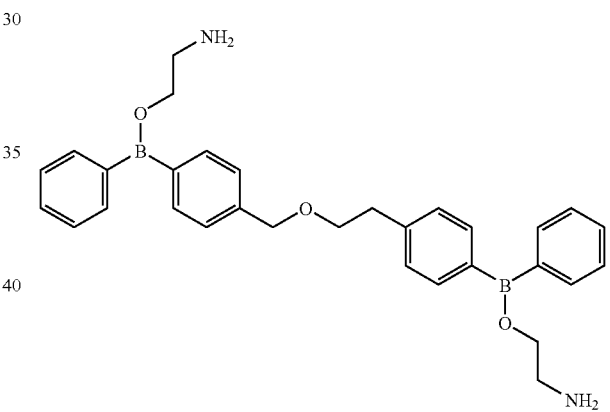

TLC: Rf 0.38 (acetonitrile:water=3:1, reverse phase); NMR (CDCl$_3$—CD$_3$OD): δ7.0–7.2 (18H, m), 4.43 (2H, s), 3.80 (4H, t, J=7 Hz), 3.65 (2H, t, J=7 Hz), 2.84 (2H, t, J=7 Hz), 2.75 (4H, t, J=7 Hz).

EXAMPLE 4(69)

[2-[(2-aminoethoxy)phenylboryl]benzyl][2-[4[(2-aminoethoxy)phenylboryl]phenyl]ethyl]ether

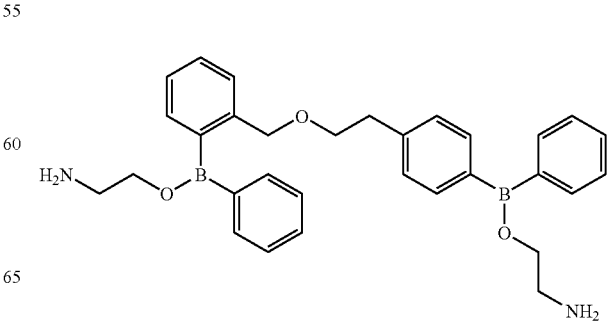

TLC: Rf 0.36 (acetonitrile:water=3:1, reverse phase); NMR (CDCl$_3$): δ6.9–7.5 (18H, m), 4.3–4.5 (2H, br), 4.22 (2H, s), 3.78 (2H, t, J=7 Hz), 3.68 (2H, t, J=6 Hz), 3.34 (2H, t, J=7 Hz), 2.79 (4H, t, J=6 Hz), 2.4–2.6 (2H, br), 1.83 (2H, br).

REFERENCE EXAMPLE 3

2-phenoxyphenylboronic acid

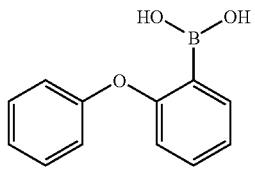

Diphenyl ether (0.85 g) was dissolved in anhydrous tetrahydrofuran (20 ml) and the reaction mixture was cooled to 0° C. N-butyllithium (1.6M, 3.1 ml) was delivered by drops thereto and the reaction mixture was stirred for 30 minutes at the same temperature. Trimethyl borate (0.68 ml) was added thereto and the reaction mixture was stirred for two hours at room temperature. 1N hydrochloric acid was added to the reaction mixture and the water layer was extracted with ethyl acetate. The organic layer was dried with anhydrous sodium sulfate. The solvent was distilled off and the obtained residue was purified by column chromatography (ethyl acetate:hexane=1.5:1 to 1:3) to obtain the title compound (304 mg) having the following physical data.

TLC: Rf 0.57 (ethyl acetate:hexane=1:3)

REFERENCE EXAMPLE 4

6-methyl-2-(2-phenoxyphenyl)-1,3,6,2-dioxy azaborocane

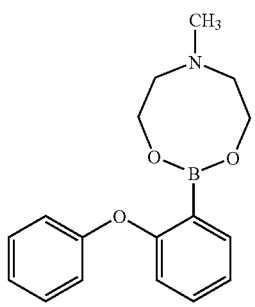

The compound produced in Reference Example 3 (304 mg) was dissolved in ethanol (10 ml) and diethanolamine (169 mg) was added thereto and the mixture was stirred for one hour at room temperature. The solvent was distilled off to obtain the title compound (403 mg) having the following physical data. NMR (CDCl$_3$): δ7.76 (1H, dd, J=7, 3 Hz), 6.7–7.3 (8H, m), 4.01 (2H, t, J=7 Hz), 3.92 (2H, t, J=7 Hz), 3.13 (4H, t, J=7 Hz), 2.64 (3H, s).

EXAMPLE 5

10H-phenoxaborin-10-ol

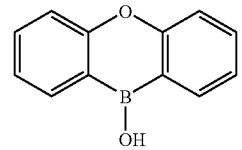

The compound produced in Reference Example 4 (0.43 g) was dissolved in anhydrous tetrahydrofuran (10 ml) and the reaction mixture was cooled to −78° C. N-butyllithium (1.6M, 0.88 ml) was delivered by drops thereto and the reaction mixture was stirred for 1.5 hours at the same temperature. Trimethyl borate (0.18 ml) was added thereto and the reaction mixture was stirred for three hours at room temperature. 1N hydrochloric acid was added to the reaction mixture and the water layer was extracted with ethyl acetate. The organic layer was dried with anhydrous sodium sulfate. The solvent was distilled off and the obtained residue was recrystallized from hexane-diisopropyl ether to obtain the title compound (87 mg) having the following physical data.

TLC: Rf 0.64 (ethyl acetate:hexane=1:1) NMR (CD$_3$OD): δ8.09 (2H, d, J=8 Hz), 7.58 (2H, t, J=8 Hz), 7.32 (2H, d, J=8 Hz), 7.22 (2H, t, J=8 Hz).

REFERENCE EXAMPLE 5

1-(4-chlorophenyl)-1-(2-bromophenyl)methanol

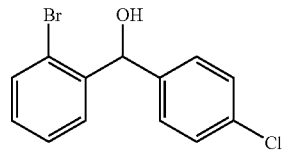

2-bromobenzaldehyde (1 ml) was dissolved in diethyl ether (20 ml) and cooled to −78° C. 4-chlorophenylmagnesium bromide (1M diethyl ether solution, 9 ml) was added thereto and the reaction mixture was stirred for one hour at the same temperature. Saturated ammonium chloride aqueous solution was added thereto and the water layer was extracted with ethyl acetate. The organic layer was dried with anhydrous magnesium sulfate. The solvent was distilled off and the obtained residue was purified by column chromatography to obtain the title compound (2.50 mg) having the following physical data.

TLC: Rf 0.62 (ethyl acetate:hexane=1:3)

REFERENCE EXAMPLE 6

3-(4-chlorophenyl)-2,1-benzoxaborol-1-(3H)-ol

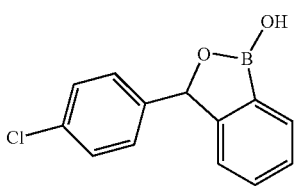

The compound produced by Reference Example 5 (508 mg) was dissolved in diethyl ether (4 ml) and cooled to 0° C. N-butyllithium (1.6M hexane solution, 2.5 ml) was delivered by drops thereto and the reaction mixture was stirred for 30 minutes at the same temperature. Tributyl borate (0.70 ml) was added thereto at −78° C. and the reaction mixture was stirred for three hours at room temperature. 1N hydrochloric acid was added to the reaction mixture and the water layer was extracted with a mixed solution of ethyl acetate-hexane (1:1). The organic layer was washed with saturated saline. The solvent was distilled off and the obtained residue was purified by column chromatography to obtain the title compound (385 mg) having the following physical data.

TLC: Rf 0.45 (ethyl acetate:hexane=1:2)

EXAMPLE 6

1,3-bis(4-chlorophenyl)-1,3-dihydro-2,1-benzoxaborole

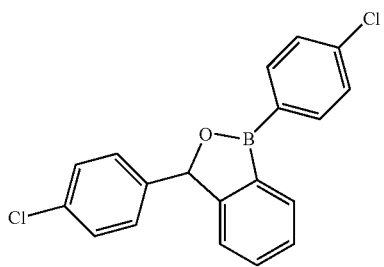

The compound produced in Reference Example 6 (231 mg) was dissolved in anhydrous tetrahydrofuran (3 ml) and cooled to −78° C. 4-chlorophenylmagnesium bromide (1M diethyl ether solution, 1.5 ml) was added thereto and the reaction mixture was stirred for three hours at room temperature. 1N hydrochloric acid was added to the reaction mixture and the water layer was extracted with diisopyl ether. The organic layer was washed with saturated saline. The solvent was distilled off and the obtained residue was purified by silica gel column chromatography to obtain the title compound of the present invention (151 mg) having the following physical data.

TLC: Rf 0.65 (hexane:ethyl acetate=3:1) NMR (CDCl$_3$): δ8.16 (3H, m), 7.46 (4H, m), 7.38–7.18 (5H, m), 6.40 (1H, s).

FORMULATION EXAMPLE

Formulation Example 1

The following components were admixed in a conventional method and punched out to give 100 tablets each containing 50 mg of active ingredient.

| | |
|---|---|
| 2-cyclohexylaminoethyl bis(3-chloro-4-methylphenyl)borate | 5.0 g |
| carboxymethylcellulose calcium (disintegrating agent) | 0.2 g |
| magnesium stearate (lubricant) | 0.1 g |
| microcrystalline cellulose | 4.7 g |

Formulation Example 2

The following components were admixed in a conventional method. The solution was sterilized in conventional method, placed 5 ml portions into ampoules and freeze-dried in conventional method to give 100 ampoules each containing 20 mg of the active ingredient.

| | |
|---|---|
| 2-cyclohexylaminoethyl bis(3-chloro-4-methylphenyl)borate | 2.0 g |
| mannitol | 20 g |
| distilled water | 500 ml |

What is claimed is:

1. A boron compound represented by the formula (I) or nontoxic salts thereof,

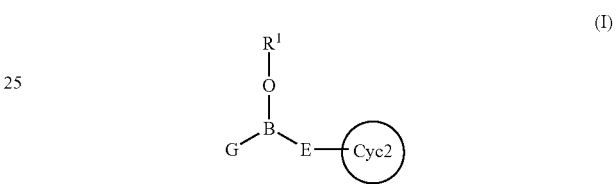

(I)

wherein $R^1$ is (1) a hydrogen atom;
(2) —(CH$_2$)$_n$—NR$^2$R$^3$, wherein n represents an integer of 1 to 3, $R^2$ and $R^3$ each independently represent, a hydrogen atom, C1–4 alkyl, mono-cyclic C5–6 carboring, or C1–4 alkyl substituted with mono-cyclic C5–6 carboring, wherein the carbon atom of —(CH$_2$)$_n$— may be substituted with 1 to 2 $R^4$, and the carboring may be further substituted with 1 to 2 $R^7$,
$R^4$ is (a) C1–8 alkyl, (b) carboxyl, (c) C1–4 alkoxycarbonyl, (d) keto, (e) mono-cyclic C5–6 carboring, (f) guanidino(C1–2)alkyl, (g) C1–6 alkyl substituted with mono-cyclic C5–6 carboring, (h) C1–2 alkyl substituted with 4-chlorophenoxy, or (i) C1–4 alkyl substituted with di(C1–4 alkyl)amino;
(3) C1–6 alkyl or C2–6 alkenyl substituted with mono-cyclic C5–6 carboring, wherein the carboring may be substituted with 1 to 5 $R^7$, and the C1–6 alkyl or C2–6 alkenyl may be further substituted with 1 to 2 $R^{10}$;
$R^{10}$ represents C1–4 alkyl or C2–4 alkenyl;
(4) —CHR$^5$R$^6$, wherein $R^5$ and $R^6$ independently represent
  (i) mono-cyclic C5–6 carboring, or
  (ii) C1–6 alkyl or C2–6 alkenyl substituted with mono-cyclic C5–6 carboring,
  wherein the carboring may further be substituted with 1 to 5 $R^7$; or
$R^7$ represents (a) C1–4 alkyl, (b) C1–4 alkoxy, (c) a halogen atom, (d) —CF$_3$, (e) nitro, (f) mono-cyclic C5–6 carboring, (g) C1–4 alkyl substituted with mono-cyclic C5–6 carboring, (h) amino, (i) —NHCO(C1–4 alkyl), or (j) C1–4 alkoxycarbonyl; G represents Cyc1;
Cyc1 represents mono- or bi-cyclic C5–10 carboring, wherein the carboring may be substituted with 1 to 5 $R^8$; Cyc2 represents mono- or bi-cyclic C5–10 carboring substituted with

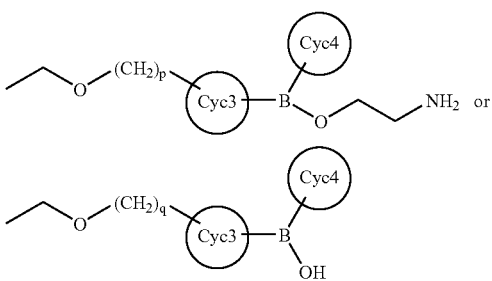

wherein the carboring may be substituted with 1 to 4 $R^9$; Cyc3 and Cyc4 independently represents mono- or bi-cyclic C5–10 carboring which may be substituted with 1 to 2 $R^7$;

$R^8$ and $R^9$ independently represents
(a) C1–4 alkyl,
(b) C2–4 alkenyl,
(c) C1–4 alkoxy,
(d) a halogen atom,
(e) —$CF_3$,
(f) C1–4 alkylthio,
(g) amino,
(h) (C1–4 alkyl)amino,
(i) di(C1–4 alkyl)amino,
(j) formyl,
(k) phenyl,
(l) phenoxy,
(m) hydroxy(C1–2)alkyl,
(n) (mono- or bi-cyclic C5–10 carboring)-O—(C1–2)alkyl,
(o) C1–4 alkoxycarbonylvinyl,
(p) C1–2 alkyl substituted with a group selected from —O—(C1–2 alkylene)-phenyl, wherein phenyl may be substituted with 1 to 3 C1–4 alkoxy, —O—CONH-phenyl, wherein phenyl may be substituted with 1 to 3 C1–4 alkyl, nitro or C1–4 alkoxycarbonyl, or —O—CONH—(C1–4) alkyl, wherein alkyl may be substituted with 1 to 3 C1–4 alkyl, carboxyl or C1–4 alkoxycarbonyl,
(q) phenylthio,
(r) —CON(C1–4 alkyl)$_2$,
(s) —$SO_2$N(C1–4 alkyl)$_2$,
(t) C1–4 alkoxy(C1–2)alkyl, or
(u) C1–4 alkoxycarbonyloxy(C1–2)alkyl, in $R^8$ and $R^9$, the carboring and phenyl may be substituted with 1 to 2 $R^7$;
p represents an integer of 1 to 4;
q represents an integer of 1 to 4; and
E represents a single bond.

2. A boron compound according to claim 1, which is
(18) bis[2-(hydroxyphenylboryl)benzyl]ether,
(19) 1,4-bis(4-(hydroxyphenylboryl)phenoxy)butane,
(20) bis[4-(hydroxyphenylboryl)benzyl]butane,
(89) bis[2-[(2-aminoethoxy)phenylboryl]benzyl]ether,
(90) bis[4-[(2-aminoethoxy)phenylboryl]benzyl]ether,
(91) [4-[(2-aminoethoxy)phenylboryl]benzyl][2-[4-[(2-aminoethoxy)phenylboryl]phenyl]ethyl]ether, or
(92) [2-[(2-aminoethoxy)phenylboryl]benzyl][2-[4-[(2-aminoethoxy)phenylboryl]phenyl]ethyl]ether, or nontoxic salt thereof.

3. A composition comprising the boron compound of formula (I) according to claim 1, or a nontoxic salt thereof and a pharmaceutically acceptable carrier.

4. A method for treatment of platelet aggregation, ischemic diseases in hearts and brains, allergosis, bronchial asthma, hypertension, cerebrovascular spasm, nephritis, pancreatitis comprising administering to a subject an effective amount of the boron compound of formula (I) according to claim 1, or a nontoxic salt thereof.

* * * * *